United States Patent
Kataoka et al.

(10) Patent No.: US 8,492,536 B2
(45) Date of Patent: Jul. 23, 2013

(54) METHOD FOR MODIFYING NUCLEIC ACID BASES, AND NUCLEIC ACID BASE-MODIFIED PRODUCT

(75) Inventors: Masanori Kataoka, Aichi (JP); Kuniaki Nagayama, Aichi (JP)

(73) Assignees: Inter-University Research Institute Corporation National Institute of Natural Sciences, Tokyo (JP); Nagayama IP Holdings, LLC, New York, NY (US)

( * ) Notice: Subject to any disclaimer, the term of this patent is extended or adjusted under 35 U.S.C. 154(b) by 577 days.

(21) Appl. No.: 12/672,649

(22) PCT Filed: Aug. 8, 2008

(86) PCT No.: PCT/JP2008/064619
§ 371 (c)(1),
(2), (4) Date: Apr. 29, 2010

(87) PCT Pub. No.: WO2009/020249
PCT Pub. Date: Feb. 12, 2009

(65) Prior Publication Data
US 2010/0222563 A1    Sep. 2, 2010

(30) Foreign Application Priority Data

Aug. 8, 2007 (JP) .................................. 2007-207083
Sep. 10, 2007 (JP) .................................. 2007-233592

(51) Int. Cl.
*C07H 21/00* (2006.01)
(52) U.S. Cl.
USPC ....... 536/25.3; 536/22.1; 536/23.1; 536/24.3; 536/25.32; 536/25.33

(58) Field of Classification Search
None
See application file for complete search history.

(56) References Cited

FOREIGN PATENT DOCUMENTS

DE     10200400997    9/2005
JP     2007-038130    2/2007

OTHER PUBLICATIONS

Tabor et al. Proc. Natl. Acad. Sci. USA (1987), vol. 84, pp. 4767-4771.*
Basu, A. K. et al, Deoxyhexanucleotide Containg a Vinyl Chloride Induced DNA Lesion, 1, N6-Ethenoadenine: Synthesis, Physical Characterization, and Incorporation into a Duplex Bacteriophage M13 Genome as Part of an amber Codon, Biochemistry, 1987, vol. 26, No. 18, pp. 5626-5635.
Jowa, L. et al., Synthesis and Characterization of Deoxyguanosine-Benzoquinone Adducts, Journal of Applied Toxicology, 1990, vol. 10, No. 1, pp. 47-54.
Krzyzosiak, W. J. et al., Long-range conformational transition in yeast tRNAPhe, induced by the Y-base removal and detected by chloroacetaldehyde modification, Nucleic Acids Research, 1983, vol. 11, No. 19, pp. 6913-6921.

* cited by examiner

*Primary Examiner* — Patrick Lewis
(74) *Attorney, Agent, or Firm* — Jordan and Hamburg LLP

(57) ABSTRACT

A method for modifying nucleic acid bases by a chemical means, which enables the discrimination of every base species in plural species of bases in a nucleic acid comprising plural nucleotide units, while retaining the base sequence information of the nucleic acid. A nucleic acid base-modified product provided by the method. The nucleic acid base-modified product is essentially a single strand. In accordance with the invention, a novel means for sequencing a nucleic acid by a microscopic means is provided.

19 Claims, 19 Drawing Sheets

FIG. 2
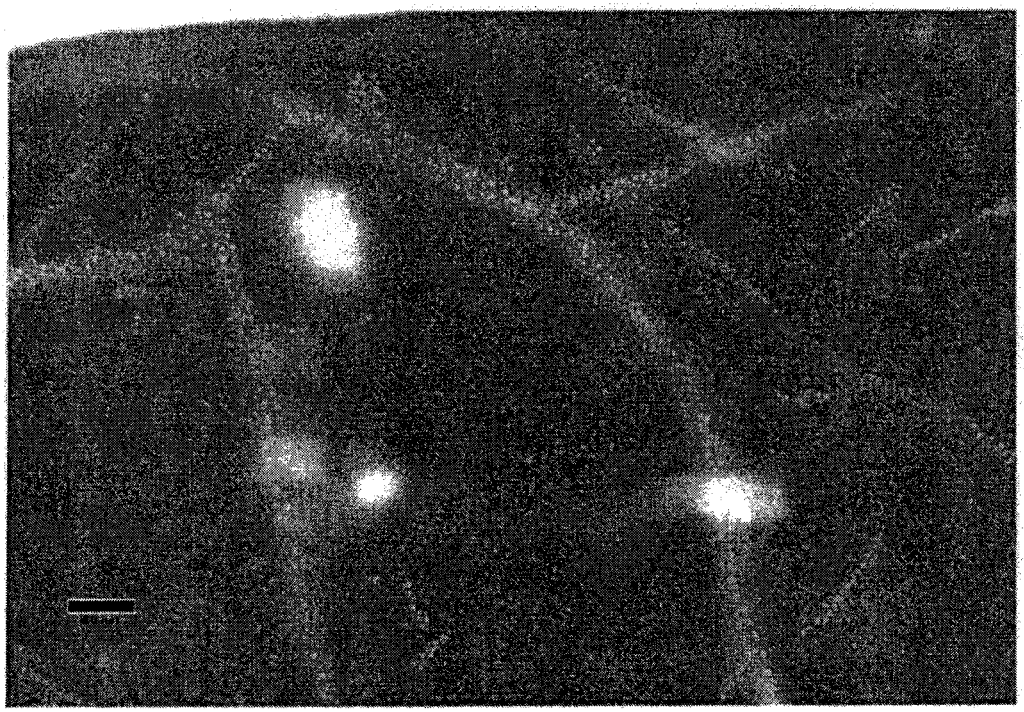
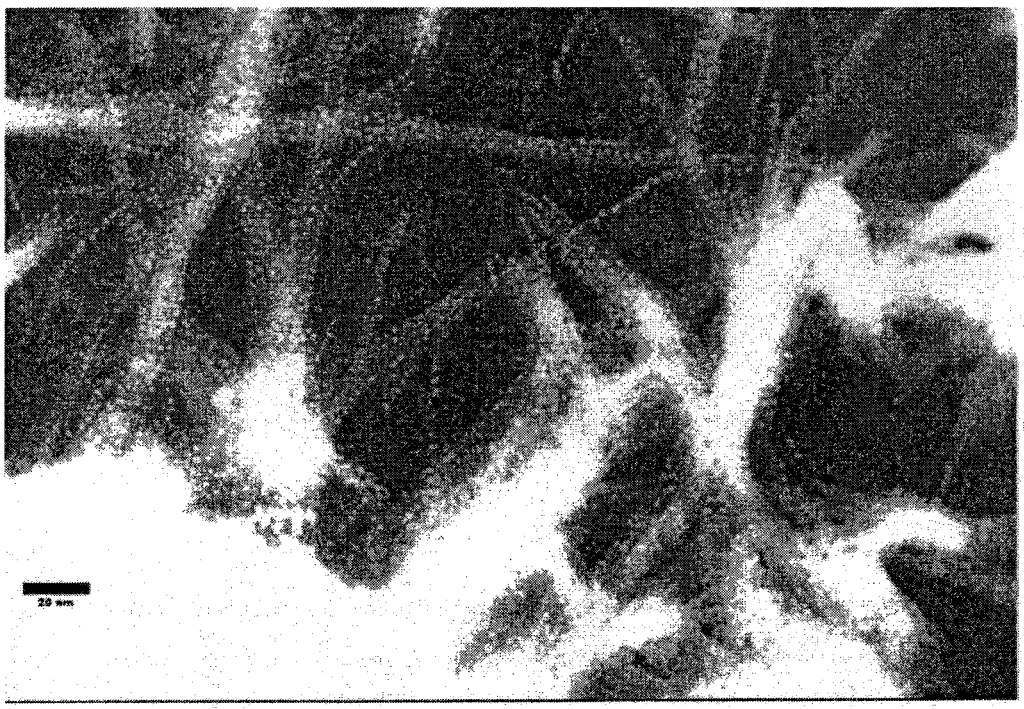

FIG. 3
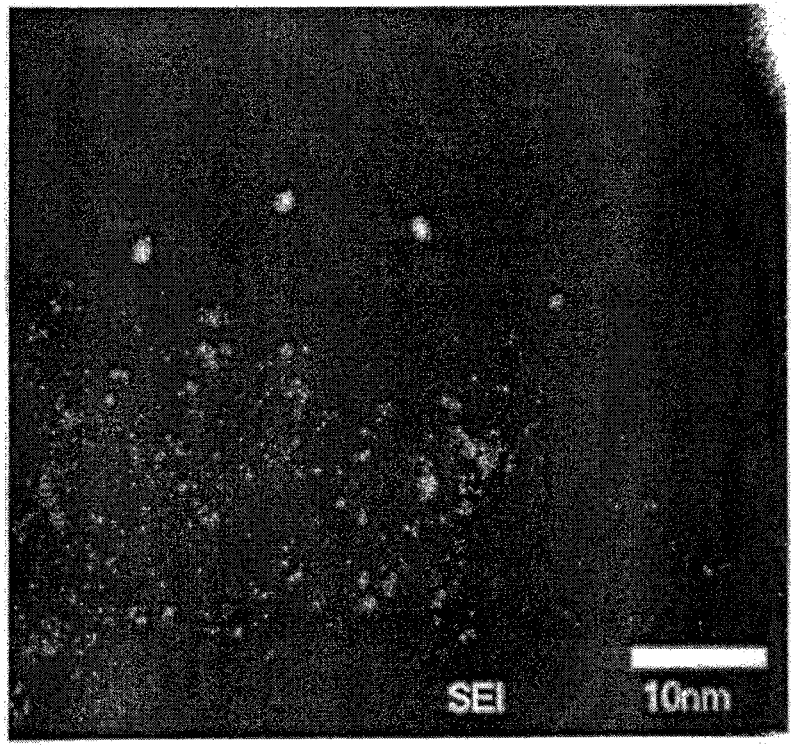
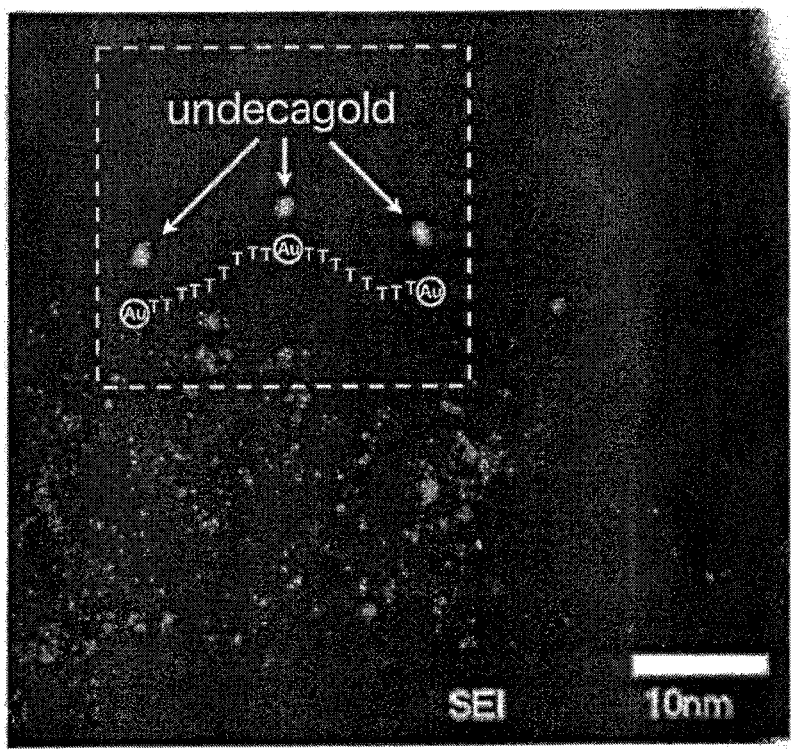

F I G. 1 5
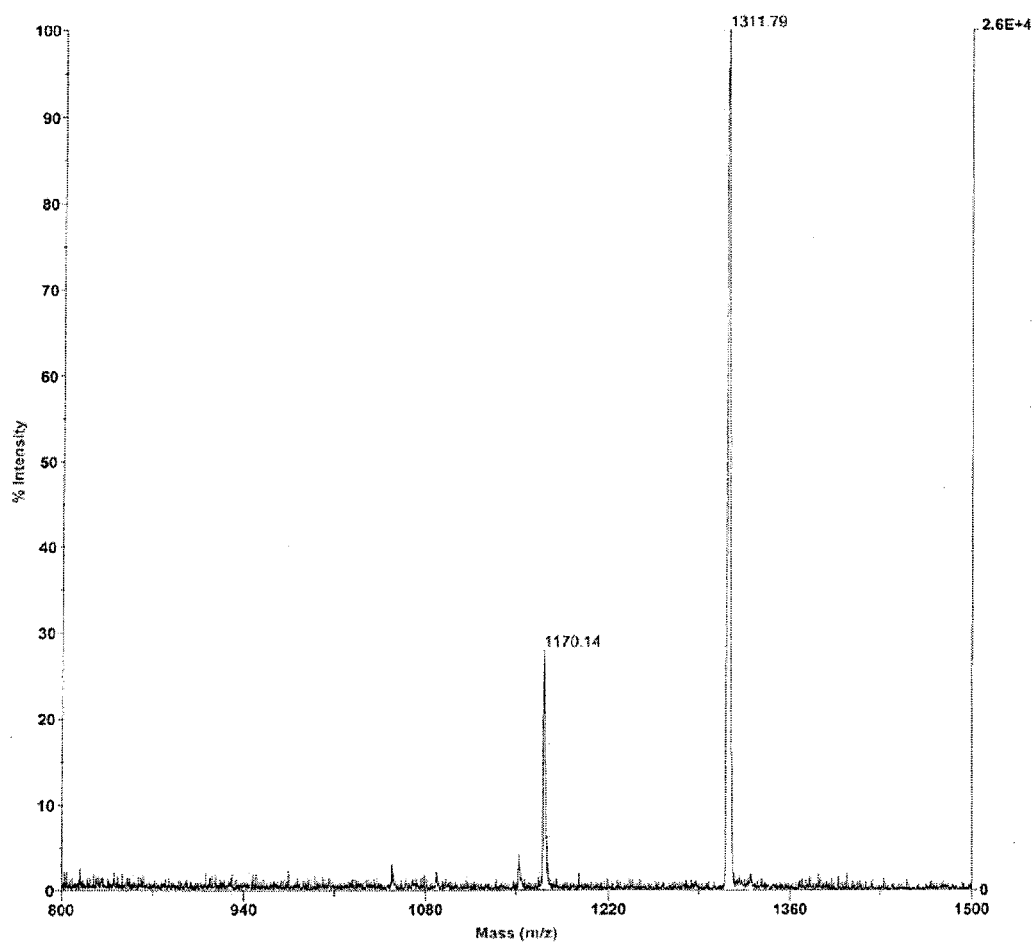

F I G. 1 8
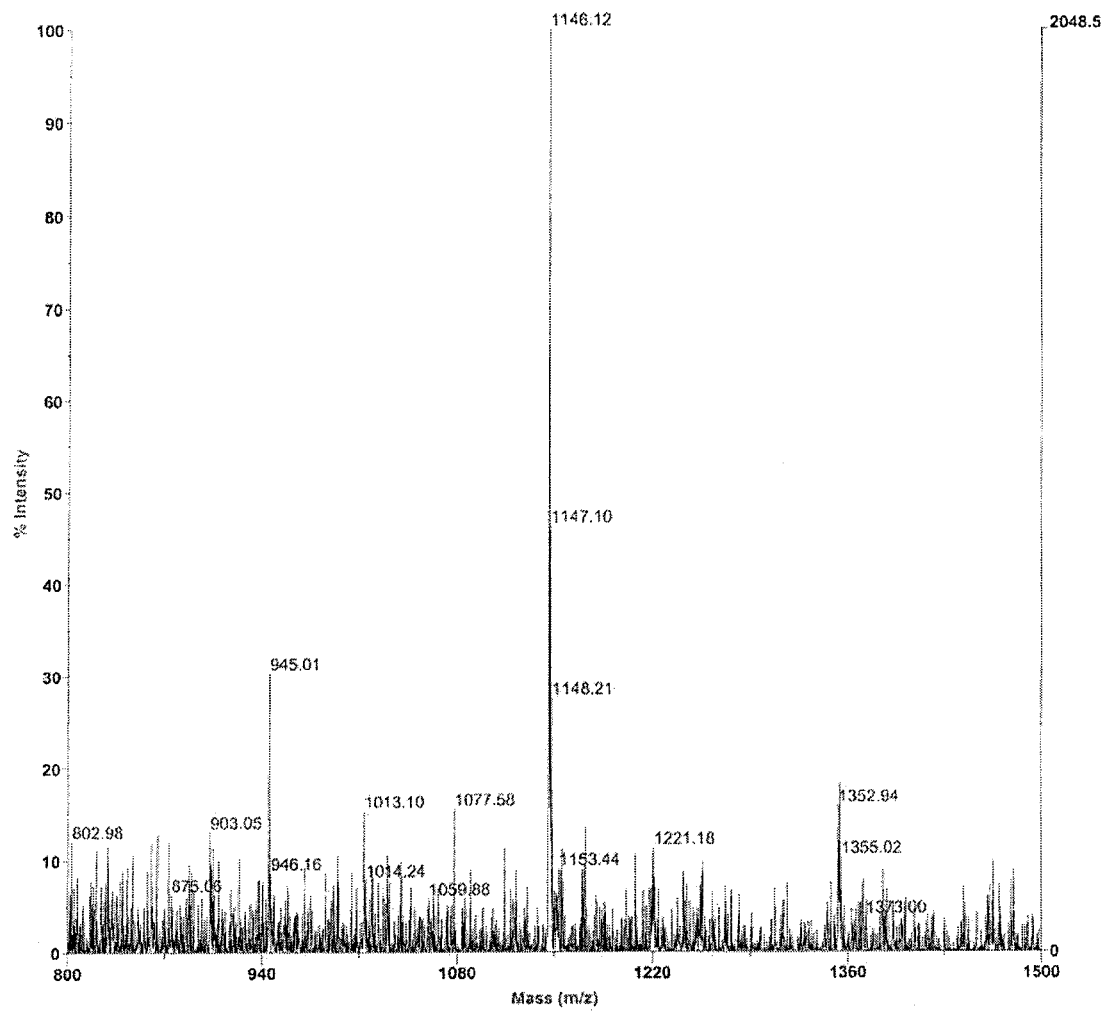

METHOD FOR MODIFYING NUCLEIC ACID BASES, AND NUCLEIC ACID BASE-MODIFIED PRODUCT

TECHNICAL FIELD

The present invention relates to a method for modifying nucleic acid bases by a chemical means, which enables the discrimination of every base species in plural species of bases in a nucleic acid comprising plural nucleotide units while retaining the base sequence information of the nucleic acid, and a nucleic acid base-modified product essentially as a single strand as provided by the method.

The method for modifying nucleic acid bases includes the substitution modification method and the enlargement modification method.

The substitution modification method is a method for substituting plural species of bases in a nucleic acid with labeling compounds by which every base species can be discriminated, comprising selectively releasing only a specific species of bases in DNA or RNA as an oligonucleotide or a polynucleotide and then incorporating a labeling compound in the sites of the released bases having existed, to obtain the sequence information of the DNA or the RNA and other information of nucleic acid bases.

The enlargement modification method is a method for structurally converting plural species of bases in a nucleic acid to bases with ring numbers by which every base species can be discriminated, comprising modifying a polynucleotide including adenine, guanine, cytosine and thymine or uracil in such a manner that these bases are modified to various base ring numbers, by which the four species of bases can be discriminated.

BACKGROUND ART

In diverse research fields and industrial fields, conventionally, an approach for simply and rapidly obtaining the sequence information of an oligonucleotide or a polynucleotide (nucleic acid) as DNA or RNA is highly needed.

Furthermore, a research and technical field called RNAi (RNA interference) starting from the discovery that a relatively short double-stranded RNA exerts a strong gene silence effect in vivo has been spread rapidly in recent years. In the field of RNAi, an approach for obtaining for example the sequence information of the double-stranded RNA as a relatively short oligonucleotide simply and rapidly has an extremely important meaning.

Conventionally, meanwhile, methods for modifying or chemically converting nucleic acid bases in a manner selective to base species have been known, like for example the well-known Maxam-Gilbert method.

Additionally, the following patent reference 1 discloses a technique for labeling the end of a reducing sugar comprising allowing for example 2-aminopyridine together with a reducing agent to react with the end thereof.

[Reference 1] JP-A-2007-038130

By the Maxam-Gilbert method, however, only a single nucleic acid base in a subject nucleic acid chain is released; subsequently, the chain is cleaved starting from the site under basic conditions. By the method, therefore, not all of the bases of one nucleic acid base species in the subject nucleic acid chain are substituted and labeled.

Further, the patent reference 1 discloses one type of sugar chain-labeling techniques for simply labeling the end of a reducing sugar through a reducing amination. As an elemental technique, the patent reference 1 has some relation with the object of the invention but essentially, the patent reference 1 does not have much relation with the invention.

Alternatively, the reaction of a poly- or oligodeoxyribonucleotide including adenine, guanine, cytosine and thymine or a poly- or oligoribonucleotide including adenine, guanine, cytosine and uracil with chloroacetaldehyde to modify the adenine and the cytosine therein has been known (the following reference 2). Such modified nucleosides have a property of emitting fluorescence and are converted to monomers for use with an automatic oligonucleotide synthetic apparatus; and then, the monomers are incorporated into an oligonucleotide with the synthetic apparatus for use as a fluorescent nucleic acid probe and the like (the following reference 3).

[Reference 2] Biochemistry, vol. 11, No. 19, 3499-3506 (1972)

[Reference 3] Biochemistry, vol. 26, No. 19, 5626-5635 (1987)

Although the method of the reference 2 is a simple and secure method, the method is used just for modifying only adenine and cytosine. By the method alone, thus, all bases constituting DNA or RNA cannot be discriminated.

The group of the present inventors has made examinations about the analysis of DNA and RNA sequences with an electron microscope by labeling bases constituting DNA and RNA. A method for labeling individual bases constituting DNA and RNA in a simple manner has been demanded.

DISCLOSURE OF THE INVENTION

It is an object of the invention to develop a method for modifying nucleic acid bases in such a manner that every base species can be discriminated from each other, by which the quantitative analysis of the number of bases in a nucleic acid can be done and the information of the distribution of the bases can be obtained, along with the detection of spontaneously modified bases, and also to provide the resulting modified nucleic acid.

[Reference 4] A. Chemea, et al., "Large Scale Synthesis of p-Benzoquinone-2'-Deoxycytidine and p-Benzoquinone-2'-Deoxyadenosine Adducts and Their Site-Specific Incorporation into DNA Oligonucleotides", Chem. Res. Toxicol. 8, 865-874 (1995)

[Reference 5] Lubow Jowa, et al., "Synthesis and Characterization of Deoxyguanosine-Benzoquinone Adducts", JOURNAL OF APPLIED TOXICOLOGY, vol. 10, No. 1, 47-54 (1990)

For the purpose of actually detecting nucleic acid bases never discriminated by conventional analytical techniques, the inventor invented a method for modifying a nucleic acid (substitution modification method) by which the sequence information of the nucleic acid and the like could be obtained by utilizing conventional analytical techniques, comprising chemically treating the nucleic acid bases to substitute the nucleic acid bases with labeling compounds enabling the discrimination of every base species in the nucleic acid bases.

Then, the inventor made detailed examinations about the method for modifying DNA with chloroacetaldehyde as described in the reference 2. Consequently, the inventor found via the modification of the reaction conditions that guanine never modified by the method could be modified with similar halogenated carbonyl compounds or benzoquinone compounds (the reference 4 and the reference 5). The inventor found that using two types of halogenated carbonyl compounds or one halogenated carbonyl compound type, polynucleotides were modified in two steps or three steps including selective release of specific bases, via the modification of the reaction conditions, so that adenine and cytosine were modified with a first halogenated carbonyl compound and guanine was modified with a second halogenated carbonyl compound or a benzoquinone compound. Consequently, the resulting polynucleotide was structurally composed of the modified adenine, the modified guanine and the modified cytosine and unmodified thymine or uracil, so that the constitutive bases could be discriminated. Via the detailed examination of the reaction conditions with the benzoquinone compound, adenine and cytosine were selectively modified, so that the constitutive bases could be discriminated (the enlargement modification method).

(First Invention)

In a first aspect, the invention relates to a method for modifying nucleic acid bases in such a manner that every base species in plural species of bases in a nucleic acid as an oligonucleotide or a polynucleotide can be discriminated while retaining the base sequence of the nucleic acid.

In the first aspect and the following individual aspects of the invention, the phrase "modifying nucleic acid bases in such a manner that every base species can be discriminated" means modifying for example a purine base and a pyrimidine base in various manners such that the purine base and the pyrimidine base can be discriminated from each other or means that adenine, guanine, cytosine and thymine (or uracil) for example are modified in various manners such that these bases can be discriminated from each other. Additionally, such modification is particularly preferably done for all of specific species of plural bases contained in a nucleic acid, namely at a probability of 100%. So as to substantially achieve the objects of the invention, the modification may satisfactorily be done preferably at a probability of 95% or more, more preferably at a probability of 99% or more.

(Second Invention)

In a second aspect, the invention relates to a method for modifying nucleic acid bases in the first aspect of the invention, where plural species of bases in a nucleic acid are modified by the following means (1) or (2) in such a manner that every base species therein can be discriminated.
(1) Base substitution reaction.
(2) Enlargement reaction of base ring structure.

(Third Invention)

In a third aspect, the invention relates to a nucleic acid base-modified product produced by modifying a single-stranded nucleic acid as an oligonucleotide or a polynucleotide as a subject for the analysis of the base sequence in such a manner that every base species in plural species of bases can be discriminated by the method in accordance with the first or second aspect of the invention.

(Fourth Invention)

In a fourth aspect, the invention relates to a method for modifying nucleic acid bases comprising selectively releasing a specific species of bases among plural species of bases in a nucleic acid comprising plural nucleotide units and then incorporating one single type of a labeling compound in the sites of these bases having been bound.

In the fourth aspect of the invention, the selective release of the specific species of bases and the incorporation of the labeling compound are particularly preferably done at a probability of 100% for such specific species of plural bases contained in the nucleic acid. For substantially achieving the objects of the invention, the selective release and the incorporation may satisfactorily be done, preferably at a probability of 95% or more, more preferably at a probability of 99% or more.

(Fifth Invention)

In a fifth aspect, the invention relates to a method for modifying nucleic acid bases in the fourth aspect of the invention, comprising repeating the processes of the method for modifying nucleic acid bases for every base species in plural species of bases in a nucleic acid and then incorporating labeling compounds of different types depending on the base species, by which every base species can be discriminated from each other and can be detected.

(Sixth Invention)

In a sixth aspect, the invention relates to a method for modifying nucleic acid bases in the fourth or fifth aspect of the invention, where the plural species of bases are bases of two types, namely purine bases encompassing at least adenine and guanine and pyrimidine bases encompassing at least cytosine, thymine and uracil.

(Seventh Invention)

In a seventh aspect, the invention relates to a method for modifying nucleic acid bases in any one of the fourth to sixth aspects of the invention, where the means for selectively releasing a specific species of bases includes at least any one or more of the following means.
(1) For the selective release of purine bases, a method using H-type cation exchange resins, strong acids, or strong acids in the co-presence of methylation agents for the release.
(2) For the selective release of pyrimidine bases, a method using hydrazine, or methylhydrazine for the release.
(3) For the selective release of guanine, a method using Louise acids, or strong acids in the presence of methylation agents for the release.
(4) For the selective release of adenine, a method using any ion exchange resin of HCOOH type, HCl type, $CH_3COOH$ type, $C_6F_5OH$ type, $CCl_2COOH$ type, $CCl_3COOH$ type or —$SO_3H$ type for the release, or a method comprising the treatment with aqueous 0.1- to 1 M strong acid solutions. The strong acid includes at least hydrochloric acid, sulfuric acid and nitric acid.
(5) For the selective release of cytosine, a method using mixtures of Louise acids and strong acids for the release, or a method comprising alkylating or acylating the amino group of cytosine and then subjecting the resulting product to a strong acid, or a method comprising interaction with hydrazine in the presence of NaCl.
(6) For the selective release of thymine or uracil, a method comprising alkylating or sulfonylating the C=O bond at position 4 or a method comprising harmonized cyclization of the C=C bond at positions 5 and 6 with ethylene or acetylene compounds.

(Eighth Invention)

In an eighth invention, the invention relates to a method for modifying nucleic acid bases in any one of the fourth to seventh aspects of the invention, where the means for incorporating a labeling compound is a reducing amination of the hydroxyl group in the site from which a base has been released with a labeling amino compound.

(Ninth Invention)

In a ninth aspect, the invention relates to a method for modifying nucleic acid bases in the eighth aspect of the invention, where the labeling amino compound is monoaminoundecagold.

(Tenth Invention)

In a tenth aspect, the invention relates to a method for modifying nucleic acid bases in the eighth aspect of the invention, where the labeling amino compound is an aminoethanol as a linker for label incorporation as bound to a label, or 1-aminomethylpyrene as a fluorescent dye, quantum dots, spin labels containing at least TEMPO, organic dyes including at least TET, or fluorescent proteins.

(Eleventh Invention)

In an eleventh aspect, the invention relates to a nucleic acid base-modified product of a polynucleotide comprising adenine (A), guanine (G), cytosine (C) and thymine (T) or uracil (U), where the adenine is converted to a modified adenine represented by the following general formula:

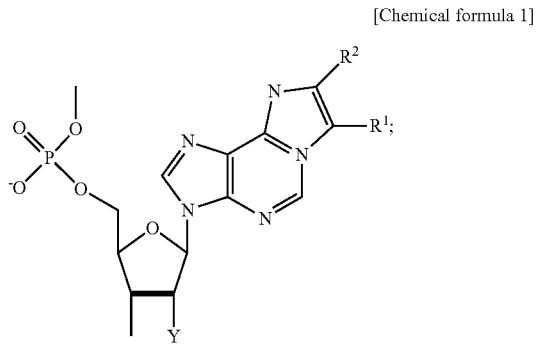

[Chemical formula 1]

the guanine is converted to a modified guanine represented by the following general formula:

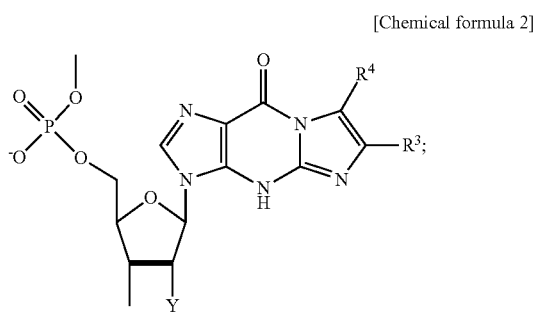

[Chemical formula 2]

the cytosine is converted to a modified cytosine represented by the following general formula:

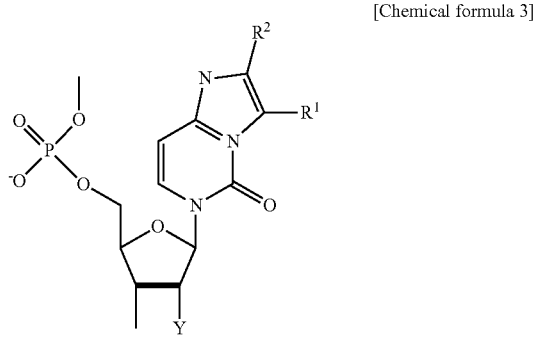

[Chemical formula 3]

(in the formulas, $R^1$ to $R^4$ individually represent hydrogen atom or a hydrocarbon group; $R^1$ and $R^2$ together may form a 5-membered or 6-membered ring; $R^3$ and $R^4$ together may form a 5-membered or 6-membered ring; herein, $R^1$ and $R^2$ differ from $R^3$ and $R^4$; and Y represents hydrogen atom or hydroxyl group).

(Twelfth Invention)

In a twelfth aspect, the invention relates to a nucleic acid base-modified product, where the modified adenine or the modified guanine in the eleventh aspect of the invention is converted to a modified product represented by the following general formula:

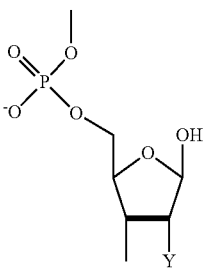

[Chemical formula 4]

(in the formula, Y represents the same meaning as described above).

(Thirteenth Invention)

In a thirteenth aspect, the invention relates to a method for modifying nucleic acid bases so as to produce a nucleic acid base-modified product in the eleventh aspect of the invention, comprising a step of allowing a first halogenated carbonyl compound represented by the following general formula:

$$CHClR^1COR^2$$

(in the formula, $R^1$ and $R^2$ individually represent hydrogen atom or a hydrocarbon group; and $R^1$ and $R^2$ together may form a 5-membered or 6-membered ring) to react with a polynucleotide comprising adenine (A), guanine (G), cytosine (C) and thymine (T) or uracil (U) in an aqueous solution and a step of allowing a second halogenated carbonyl compound represented by the following general formula:

$$CHXR^3COR^4$$

(in the formula, $R^3$ and $R^4$ individually represent hydrogen atom or a hydrocarbon group; $R^3$ and $R^4$ together may satisfactorily form a 5-membered or 6-membered ring provided that $R^3$ and $R^4$ differ from $R^1$ and $R^2$; X represents Br, I or an alkylsulfonate ester) or a p-benzoquinone derivative represented by the general formula of the following chemical formula 5 ($R^5$, $R^6$ and $R^7$ individually represent hydrogen atom or a hydrocarbon group; $R^5$ and $R^6$ together may satisfactorily form a 5-membered or 6-membered ring) to react with the resulting product in an aqueous solution adjusted to pH 2.0 to 4.5.

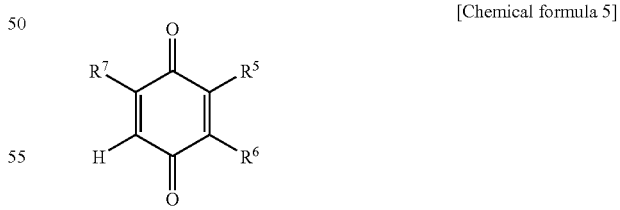

[Chemical formula 5]

(Fourteenth Invention)

In a fourteenth aspect, the invention relates to a method for modifying nucleic acid bases in the thirteen aspect of the invention for producing a nucleic acid base-modified product described in the twelfth aspect of the invention, further comprising a step of adjusting the pH to 4.5 to 7.0.

(Fifteenth Invention)

In a fifteenth aspect, the invention relates to a method for modifying nucleic acid bases, where the first halogenated carbonyl compound in the thirteenth aspect or in the fourteenth aspect of the invention is chloroacetaldehyde while the second halogenated carbonyl compound in the thirteenth aspect or in the fourteenth aspect of the invention is 2-bromocyclohexanone or p-benzoquinone.

product shown by the following chemical formula 6. Herein, the chemical formula 6 is shown without (2) in the reaction scheme in FIG. 16 shown below. The method may be through the intermediate reaction step shown in the chemical formula 7.

[Chemical formula 6]

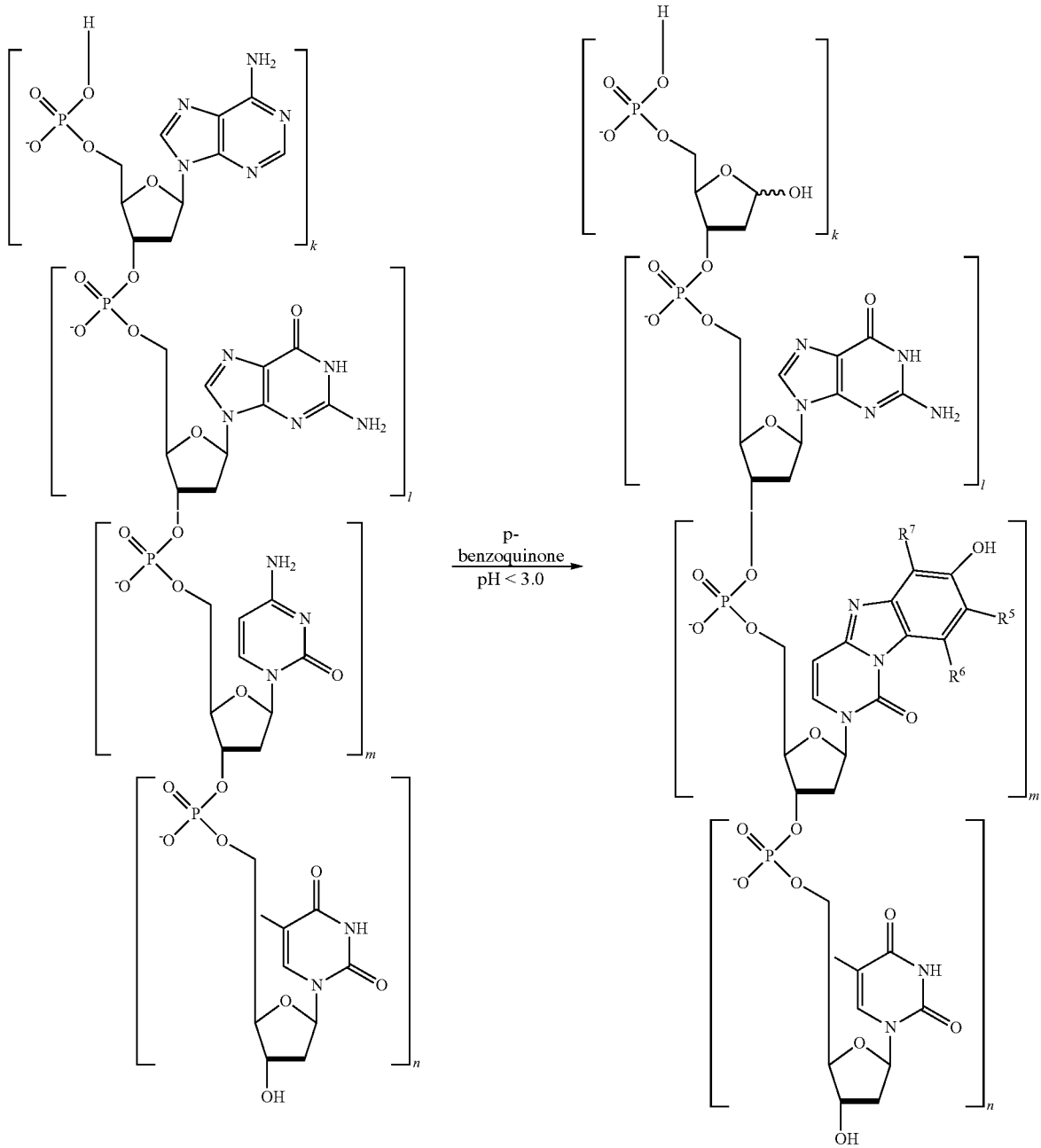

(Sixteenth Invention)

In a sixteenth aspect, the invention relates to a method for modifying nucleic acid bases, comprising treating a polynucleotide comprising adenine, guanine, cytosine and thymine or uracil with p-benzoquinone at a pH lower than pH 3.0 to induce the etheno reaction of the individual bases of adenine and cytosine and simultaneously release the resulting etheno-adenine alone, to obtain a nucleic acid base-modified In the chemical formula 6, k, l, m and n individually represent an integer of 0 or more and the total of k, l, m and n is an integer of 2 or more to 300,000,000 or less. Additionally, the order of the sequence of nucleotide units represented by k, l, m and n may be any order.

In the present specification, herein, the term "etheno reaction" means a reaction for enlarging a nucleic acid base of a natural type to an etheno base.

(Seventeenth Invention)

In a seventeenth aspect, the invention relates to a method for modifying nucleic acid bases, comprising treating a polynucleotide comprising adenine, guanine, cytosine and thymine or uracil with p-benzoquinone at a pH higher than pH 4.5 to preferentially induce the etheno reaction of adenine and cytosine to obtain a nucleic acid base-modified product shown by the following chemical formula 7.

In the following chemical formula 7, k, l, m and n individually represent an integer of 0 or more and the total of k, l, m and n is an integer of 2 or more to $3.0 \times 10^8$ or less. Herein, the order of the sequence of nucleotide units represented by K, l, m and n may be any order.

(Eighteenth Invention)

In an eighteenth aspect, the invention relates to a nucleic acid base-modified product represented by the chemical formula 6 shown in the sixteenth aspect or by the chemical formula 7 shown in the seventeenth aspect, in accordance with the invention.

(Advantages of the Invention)

In accordance with the first to eighteenth aspects of the invention, nucleic acid bases in a polynucleotide or an oligonucleotide are substituted by a simple and highly efficient chemical method to labeled compounds by which every base species in the nucleic acid bases can be discriminated, or the

[Chemical formula 7]

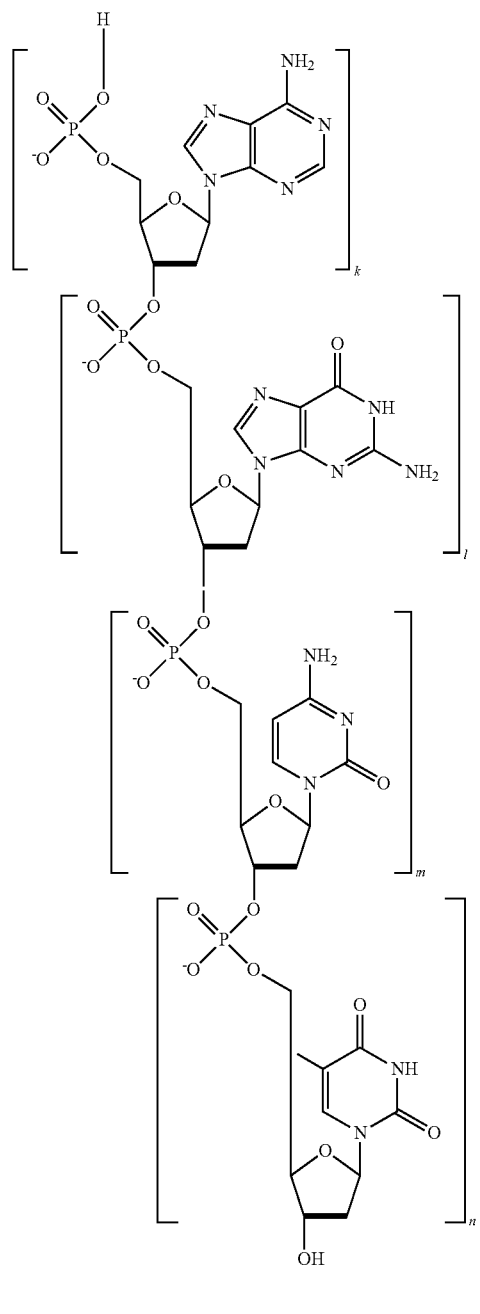
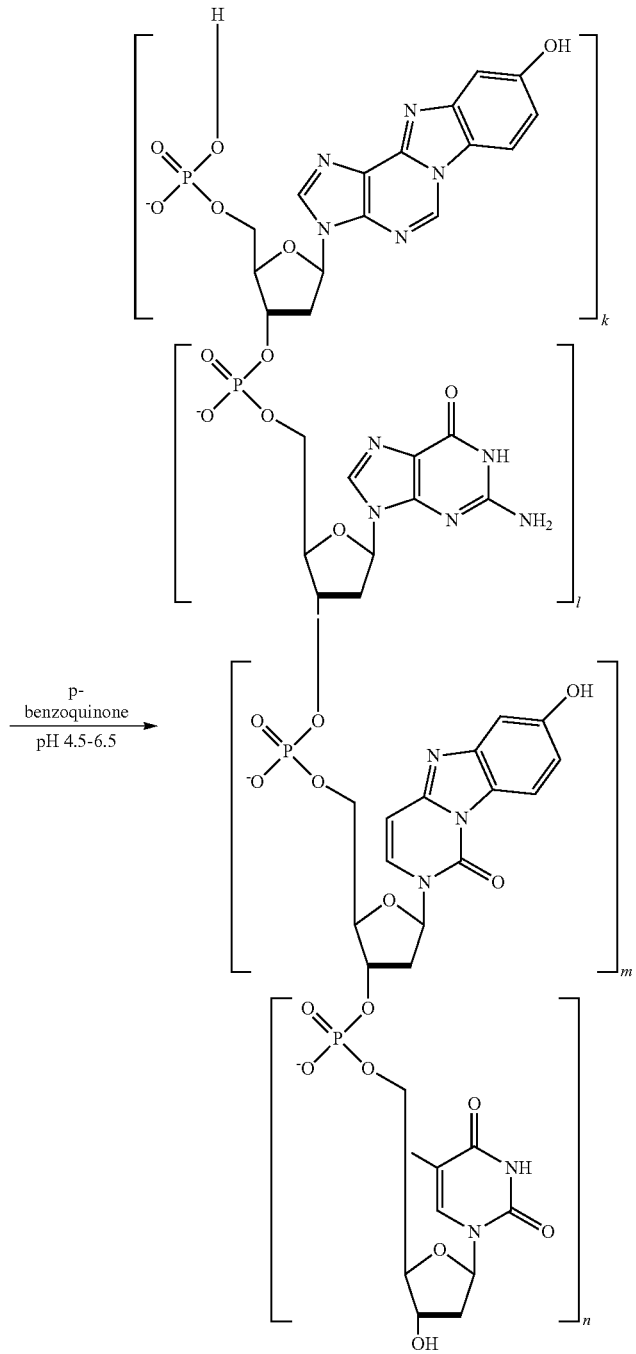

nucleic acid bases can be converted structurally in such a manner that every base species in the nucleic acid bases can be discriminated. Herein, the phrase "structurally converted in such a manner that every base species can be discriminated" means that every base species can be structurally converted so as to discriminate the difference in the size of the atom group in a base moiety by an appropriate analytical means or measurement means such as microscopic means. A typical mode of such structural conversion is a structural conversion such that every base species may have a different number of rings in the ring structure.

Thus, a nucleic acid base-modified product can be obtained from which the sequence information and the like can be obtained utilizing conventional measurement techniques. Without any deterioration of the sequence information of the polynucleotide and the oligonucleotide, the quantitative analysis of the base number can be done, while the information about the distribution and the base sequence information can be obtained, together with the detection of spontaneously modified bases.

Because the individual bases in the resulting nucleic acid base-modified product lose the property of forming complimentary base pairs via the modification, additionally, the double strand is automatically dissociated to fall into a single-stranded state essential for the unimolecular sequence analysis. In other words, laborious works such as charging an enormous amount of dissociation agents, for dissociation into a single strand and so as to resolve the intermolecular high-order configuration based on the hydrogen bond, as needed by conventional methods, are not required. Furthermore, the nucleic acid base-modified product with all the bases therein being labeled can characteristically disperse carbon nanotube more efficiently than commercially available dispersants.

In case that nucleic acid bases can be substituted and modified in a manner selective for two types of purine bases and pyrimidine bases, further, the method is effective for analyzing various nucleic acid fragments such as RNA comprising for example at least polyA sequence as described below. By the method, a nucleic acid base-modified product where all of the bases of a single species in a nucleic acid fragment such as RNA comprising at least polyA sequence for example are preliminarily substituted with a labeling compound can be obtained while retaining at least the structure of the nucleic acid (including for example information such as chain length). By utilizing such nucleic acid base-modified product, the length and quantity of the polyA sequence in mRNA can be identified and assayed, or a new possibility such as the detection of the cap structure of RNA may be obtained.

Further, the substitution modification method is highly applicable to labeling agents (labeling compounds), so that almost all of existing labels with amino group can be incorporated by the method. Practically, the multi-point labeling of an oligonucleotide with a metal cluster has successfully been achieved as described below in the Examples. Such metal cluster-labeled nucleic acids are compounds promising as programmable metal nano-wires.

By the enlargement modification method, then, individual bases can get different numbers of base rings at a single treatment, so that the individual bases are at a volume difference by about 30%. Thus, the method is extremely effective as a technique for detecting the volume difference with a microscope or by nano-pore electric current detection and the like.

All the four species of bases in a polynucleotide as modified by the enlargement modification method can be discriminated by for example the following means.

(1) A difference in the ring number causes a large difference in the volume, so that the difference in the volume can be discriminated with microscopes with size discriminating potentials, such as atomic force microscope.
(2) Furthermore, a large difference in dielectric constant is generated, so that every base species can be discriminated with transmission type electron microscopes and scanning tunneling electric current microscopes, and with apparatuses for detecting the change of electric current in pores of a nano-meter order and the like.
(3) The modified bases have fluorescence-emitting properties, so that the bases can be discriminated by detecting the fluorescent profile of a single one nucleotide unit released from the end with exonuclease or by a chemical approach.

For the discrimination, such polynucleotide or oligonucleotide should essentially be dissociated into a single strand. By the present method, the formation of base pairs is blocked via the modification, so that a nucleic acid fragment of a double strand when the method is applied is modified to a single strand automatically and additionally that no intermolecular high-order configuration based on hydrogen bond may be formed. Therefore, no dissociation agent reducing the detection sensitivity is required.

BRIEF DESCRIPTION OF THE DRAWINGS

FIG. 2 is a view depicting an image of the oligonucleotide ($dA_{20-100}$) multi-point-labeled with a gold cluster with a transmission type electron microscope (TEM). The upper image and the lower image are obtained under different fields of vision.

FIG. 3 is a view depicting an image of the oligonucleotide ($dAT_9AT_8A$) multi-point-labeled with a gold cluster by a transmission type electron microscope (TEM). The upper view is the raw view, while the lower view is a view obtained by adding explanations to the upper view.

FIG. 15 shows the mass spectrum of the oligonucleotide after the modification at the third step in the third example group.

FIG. 18 shows a mass spectrum of the oligonucleotide after the modification at the second step in Example 1 in the fourth example group.

MODES FOR CARRYING OUT THE INVENTION

Figure 1:
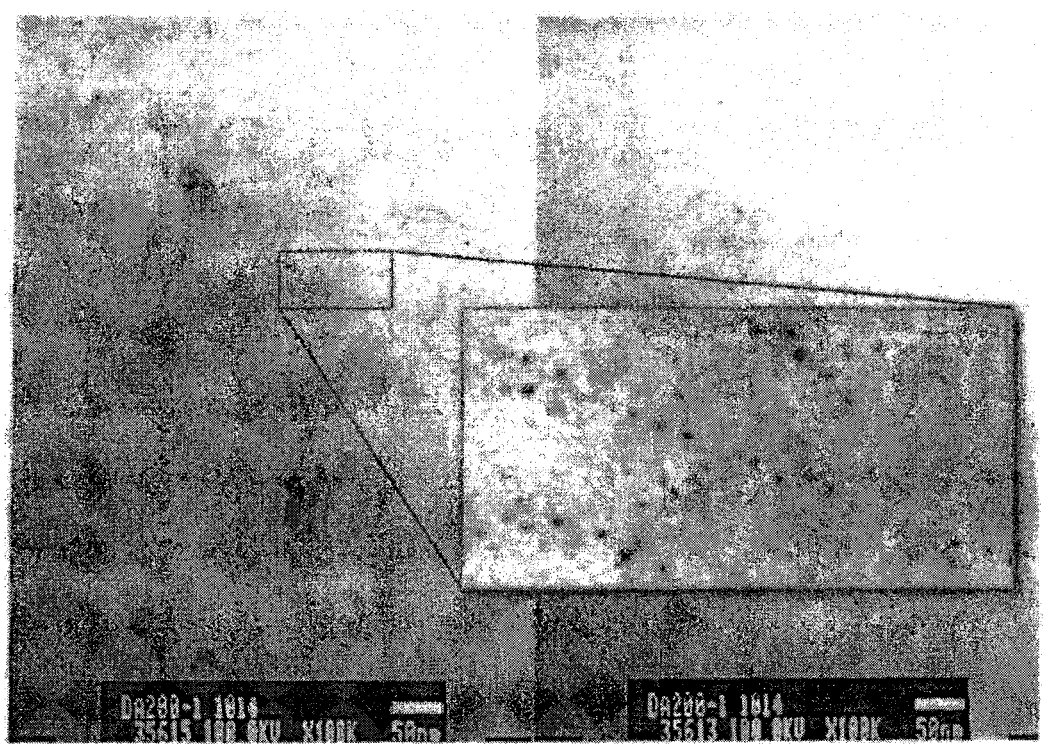
FIG. 1 is a view depicting an image of the oligonucleotide ($dA_{20}$) multi-point-labeled with a gold cluster with a transmission type electron microscope (TEM).

Modes for carrying out the invention including the best mode therefor are now described. The technical scope of the invention is never limited by these modes.

(First Mode of the Substitution Modification Method)

The first mode of the substitution modification method is summarized in the general formula of the chemical formula 8 below. First, a natural nucleic acid base or a non-natural nucleic acid base shown as "B" in the formula is released by allowing an appropriate base release means to interact with such base to generate a ribose residue of the hemi-acetal type; subsequently, a labeling compound represented as the word "LABEL" is incorporated in the site of the base having been bound by a reducing amination and the like, while involving the ring opening of the ribose ring.

As to the labeling compound, almost all of existing labeling compounds can be incorporated. For example, a compound with primary or secondary amino group can be incorporated. Additionally, the substitution of a nucleic acid base with such labeling compound can inhibit the formation of any molecular multi-dimensional configuration or a double strand based on base-pair formation, to prepare a single-stranded nucleic acid with no multi-dimensional structure within the molecule. By giving inter-chain interactions or binding differing from base-pair formation, otherwise, a molecular multi-dimensional configuration can be constructed or the double strand can be highly stabilized.

By the method, a nucleic acid base-modified product can be obtained, where all of a single species of bases in a nucleic acid fragment such as RNA comprising for example polyA sequence are preliminarily substituted with a labeling compound while retaining at least the structure of the nucleic acid (including the information of the chain length and the like). By utilizing such nucleic acid base-modified product, a new possibility emerges such that the length of the polyA sequence in mRNA can be indicated and the quantity thereof can be obtained or that the cap structure of RNA can be detected.

[Chemical formula 8]

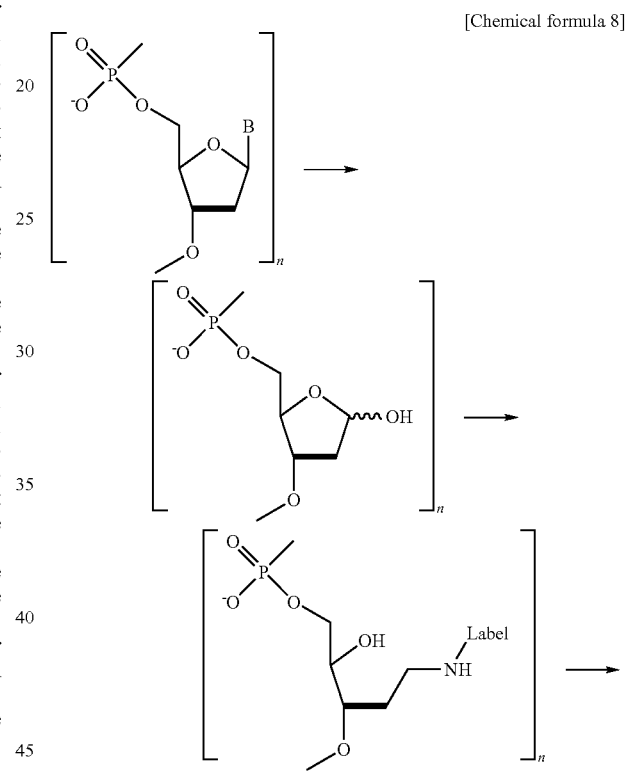

Summary of the Substitution Modification Method

The summary of the substitution modification method in the present mode is described below. Taking account of an oligonucleotide or a polynucleotide with plural or multiple repeats of the nucleotide unit shown in the general formula above as the chemical formula 8 excluding a specific case such as polyA sequence, generally, any one of the four species of bases is bound every nucleotide unit in a random order as the base "B" in the nucleic acid.

When a selective release means capable of selectively releasing for example adenine alone among these bases is performed, the base in the general formula as the chemical formula 8 is released instantaneously in a nucleotide unit with adenine as the base "B" in the nucleic acid. Thus, the labeling compound can be incorporated instantaneously in only these nucleotide units.

By allowing a selective release means capable of selectively releasing for example guanine alone to interact with the nucleic acid on completion of the above process, a labeling compound can be incorporated instantaneously in only nucleotide units with guanine as the base "B" in the nucleic acid. In that case, different types of labeling compounds can be incorporated, by which adenine and guanine can be discriminated from each other for detecting adenine and guanine.

By repeating such processes, all of the four species of bases in a nucleic acid can be substituted with labeling compounds differing from each other depending on every base species. The same is true with a case that all of the four bases are not contained in a nucleic acid. Besides, a selective release means capable of selectively releasing for example purine bases and pyrimidine bases is allowed to react with a nucleic acid, so that all of the two types of such bases may be substituted with labeling compounds differing from each other depending on the two types of bases.

By the method, a nucleic acid base-modified product where all of the four species of bases in a nucleic acid are substituted with labeling compounds can be obtained, where each of the labeling compounds is specific to each of the base species, while retaining the structure of the nucleic acid (including abundant information about for example the chain length, the sequence information, and the content of each of the base species).

Utilization of the Nucleic Acid Base-Modified Product

By utilizing such nucleic acid base-modified product, for example, those described below can be achieved.

(1) In case that labeling compounds with different sizes depending on every base species are incorporated, measurement techniques for size detection, for example, atomic force microscopy can achieve the technique for analyzing the unimolecular sequence of a nucleic acid.

(2) In case that labeling compounds with different dielectric constants depending on every base species are incorporated, measurement techniques for measuring dielectric constant with for example scanning tunneling electric current microscope and apparatuses for measuring nanopore electric current and the like can achieve the technique for analyzing the unimolecular sequence of a nucleic acid.

(3) In case that labeling compounds with different fluorescence emission properties depending on every base species are incorporated, techniques for analyzing the unimolecular sequence of a nucleic acid can be achieved with exonucleases of nucleic acids, electrophoresis, and fluorescence detection.

(4) In case that clusters of different metal species depending on every base species are incorporated, a conductor of a line width of 1 nm or less under controls of the conductivity with a nucleic acid sequence can be achieved; when branched RNA is used as a raw material together with a semiconductor metal as a labeling agent, an electric circuit can be prepared.

In accordance with the invention, the term "nucleic acid" means an oligonucleotide or a polynucleotide comprising plural nucleotide units. The term "plural" means numerical figures of two or more. Nucleic acid encompasses DNA and RNA, and also encompasses DNA and RNA of single stands and double strands or more strands. Particularly, single-stranded DNA and RNA are preferable.

Means for Selectively Releasing Bases

The means for selectively releasing bases of a specific species in a nucleic acid includes at least any one of the following means. Particularly preferably, the means includes a combination of two or more of these means.

(1) For the selective release of a purine base, a method using H-type cation exchange resins, strong acids, or strong acids in the co-presence of methylation agents for the release.

(2) For the selective release of a pyrimidine base, a method using hydrazine, or methylhydrazine for the release.

(3) For the selective release of guanine, a method using aluminium chloride or tin chloride, Louise acids such as trimethylsilyltriflic acid, or methyl iodide, dimethylsulfuric acid, hydrochloric acid, dimethylsulfuric acid with dimethylsulfate buffer, and aqueous solutions of sulfuric acid and nitric acid. The dilute aqueous solutions are at a concentration of 0.05 M or less.

(4) For the selective release of adenine, a method using any of ion exchange resins of HCOOH type, HCl type, $CH_3COOH$ type, $C_6F_5OH$ type, $CCl_2COOH$ type, $CCl_3COOH$ type or $—SO_3H$ type or a method comprising the treatment with aqueous 0.1 to 1 M strong acid solutions. The strong acid includes at least hydrochloric acid, sulfuric acid and nitric acid.

(5) For the selective release of cytosine, a method using mixtures of Louise acids and strong acids, a method comprising alkylating or acylating the amino group of cytosine to subject the resulting product to strong acids, and a method comprising reaction with hydrazine in the presence of NaCl.

(6) For the selective release of thymine or uracil, a method comprising alkylating or sulfonating the C=O bond at position 4 or a method comprising harmonized cyclization of the C=C bond at positions 5 and 6 with ethylene or acetylene compounds.

Types of Labeling Compounds and Incorporation Methods Thereof

As the labeling compounds for use in the mode, any labeling compound with a labeling site to be measured or detected with an appropriate known means (labeling site) and a functional moiety capable of binding to a base-released site in a nucleic acid may be satisfactory with no specific limitation.

One example of the type of preferable labeling compounds and incorporation methods is a reducing amination of the hydroxyl group in the base-released site with a labeling amino compound.

As the labeling amino compound, aminoethanol as a linker for label incorporation as bound to a label, or a fluorescent dye 1-aminomethylpyrene, quantum dots and organic dyes including at least TET, spin labels containing at least TEMPO or fluorescent proteins are preferably used.

Additionally when the known monoaminoundecagold is used as such labeling amino compound, the labeling progress can be observed under TEM. The reaction scheme in this case is shown below in the chemical formula 9. In the chemical formula 9, "Au" means a label of a metal cluster, namely amino-terminated undecagold.

[Chemical formula 9]

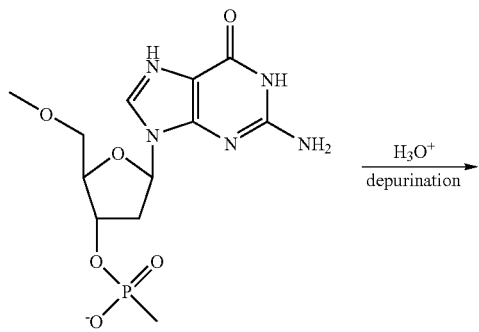

-continued

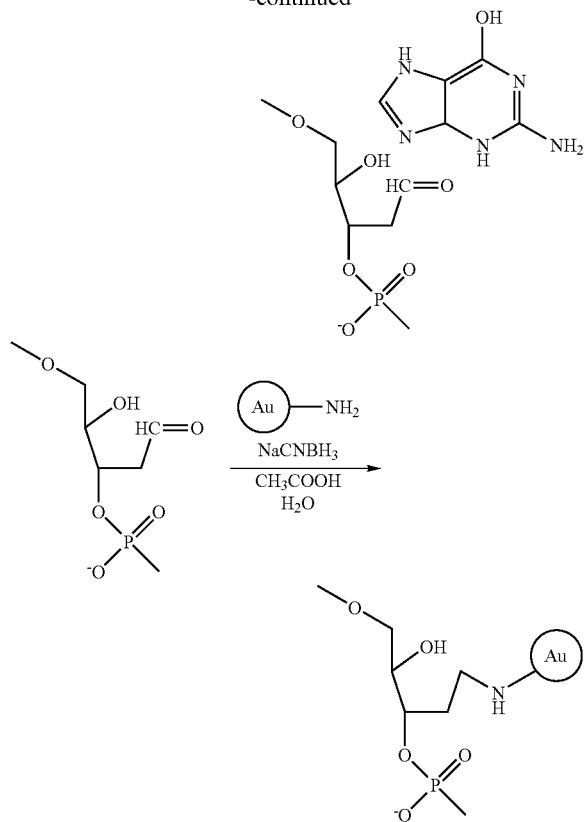

Other examples of the labeling compound type and the incorporation method include for example those described below.

Ketone and aldehydes react with primary or secondary amine in the presence of an appropriate reducing agent to generate a secondary amine or a tertiary amine (reducing amination). Reducing sugar ends and sugars primarily including riboses are in equilibrium between the ring closed structure of the hemi-acetal type and the ring opening structure of the aldehyde type. In the aldehyde type, the same reducing amination progresses.

(First Mode of the Enlargement Modification Method)

In the present mode, a polynucleotide comprising adenine (A), guanine (G), cytosine (C) and thymine (T) or uracil (U) is modified at the following two steps.

First Step:

At the step, adenine (A) and cytosine (C) are modified.

The first halogenated carbonyl compound for use in the modification is represented by the following formula.

CHClR$^1$COR$^2$

R$^1$ and R$^2$ individually represent hydrogen atom or a hydrocarbon group, preferably hydrogen atom. The hydrocarbon group includes alkyl groups and aryl groups, preferably alkyl groups. The alkyl groups include linear alkyl groups with 6 or less carbon atoms, while the aryl groups include phenyl group. Additionally, R$^1$ and R$^2$ together may form a 5-membered or 6-membered ring, preferably a 6-membered ring. The 5-membered or 6-membered ring may be an aliphatic ring or an aromatic ring, preferably an aliphatic ring.

At the step, the first halogenated carbonyl compound is allowed to react with a polynucleotide comprising adenine (A), guanine (G), cytosine (C) and thymine (T) or uracil (U).

The length of the polynucleotide to be modified is a length of 2 to $3 \times 10^8$ base pairs, preferably 20 to 3,000 base pairs.

Because the reactivity of the first halogenated carbonyl compound with such polynucleotide is lower than the reactivity of the second halogenated carbonyl compound described below, the first halogenated carbonyl compound reacts with adenine (A) and cytosine (C) to modify, but never reacts with guanine (G), thymine (T) or uracil (U) (the reference 1).

The reaction conditions are as described below.

Reaction solvents: water, water-soluble organic solvents, or mixtures of water and water-soluble organic solvents. As the water-soluble organic solvents, methanol, or ethanol, DMF, DMSO, dioxane, acetone, acetonitrile, dimethylcarbonate, ethylene carbonate, ethylene glycol, and diethylene glycol are preferable.

Polynucleotide concentration: 1 μM to 100 mM (particularly preferably 0.1 mM on a nucleic acid base concentration basis)

Concentration of the first halogenated carbonyl compound: 0.1 M to 2.0 M (particularly preferably 0.1 M)

pH: 4 to 7 (particularly preferably pH 5.5)

Reaction temperature: 20 to 45° C. (particularly preferably 37° C.)

Reaction time: 1 to 144 hours (particularly preferably 72 hours)

The pH adjustment is done, using various amines primarily including triethylamine, various buffers such as carboxylate buffers primarily including acetate buffer, formate buffer and phosphate buffer. Sodium acetate buffer is particularly preferable.

Via the reaction, adenine (A) in the polynucleotide is modified as follows.

[Chemical formula 10]

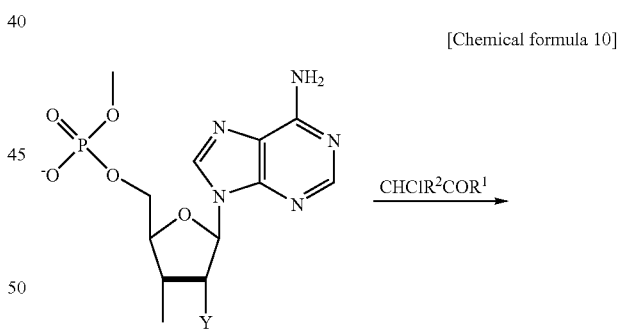

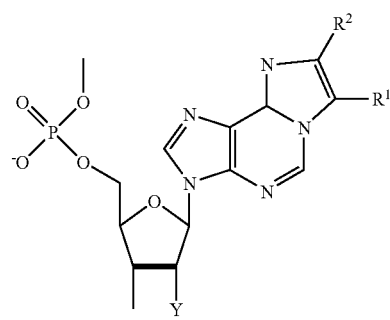

Additionally, cytosine (C) in the polynucleotide is modified as follows.

[Chemical formula 11]

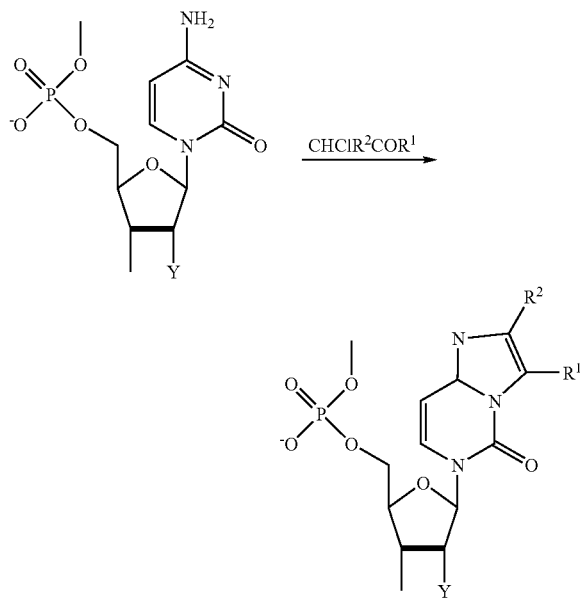

Second Step:

At the step, guanine (G) is modified.

The second halogenated carbonyl compound for use in the modification is represented by the following formula.

CHXR³COR⁴

R³ and R⁴ individually represent hydrogen atom or a hydrocarbon group. As the hydrocarbon group, alkyl groups and aryl groups are listed. Alkyl groups are preferable. The alkyl groups include for example linear alkyl groups with 6 or less carbon atoms. The aryl groups include phenyl group. Further, R³ and R⁴ together may satisfactorily form a 5-membered or 6-membered ring, preferably a 6-membered ring. The 5-membered or 6-membered ring may be an aliphatic ring or an aromatic ring. Aliphatic rings are preferable. X represents Br, I or an alkylsulfonate ester. The alkyl group of the alkylsulfonic acid includes for example methyl group, ethyl group, trifluoromethyl group, phenyl group and mesityl group.

Herein, R³ and R⁴ differ from R¹ and R². In other words, the case that R³ is R¹ and R⁴ is R² and the case that R³ is R² and R⁴ is R¹ are excluded.

At the step, the second halogenated carbonyl compound is allowed to react with the polynucleotide with modified adenine (A) and modified cytosine (C) at the first step. Because the reactivity of the second halogenated carbonyl compound with such polynucleotide is higher than the reactivity of the first halogenated carbonyl compound described above, guanine (G) never modified at the first step reacts with the second halogenated carbonyl compound for modification. Like the first halogenated carbonyl compound, the second halogenated carbonyl compound never reacts with thymine (T) or uracil (U).

The reaction conditions are as described below.

Reaction solvent: water, water-soluble organic solvents, or mixtures of water and water-soluble organic solvents. As the water-soluble organic solvents, methanol, or ethanol, DMF, DMSO, dioxane, acetone, acetonitrile, dimethylcarbonate, ethylene carbonate, ethylene glycol, and diethylene glycol are, preferable.

Polynucleotide concentration: 1 μM to 100 mM

Concentration of the second halogenated carbonyl compound: 0.1 M to 2.0 M pH: 4 to 7

Reaction temperature: 0 to 65° C.

Reaction time: 1 to 144 hours

The pH adjustment is done, using various amines primarily including triethylamine, various buffers such as carboxylate buffers primarily including acetate buffer, formate buffer and phosphate buffer.

Via the reaction, guanine (G) in the polynucleotide is once modified with the second halogenated carbonyl compound, but the resulting compound is so relatively unstable that the base is eliminated under general conditions (for example, pH 4 or less and the temperature of 25° C.).

At the step, guanine (G) in the polynucleotide is modified as follows.

[Chemical formula 12]

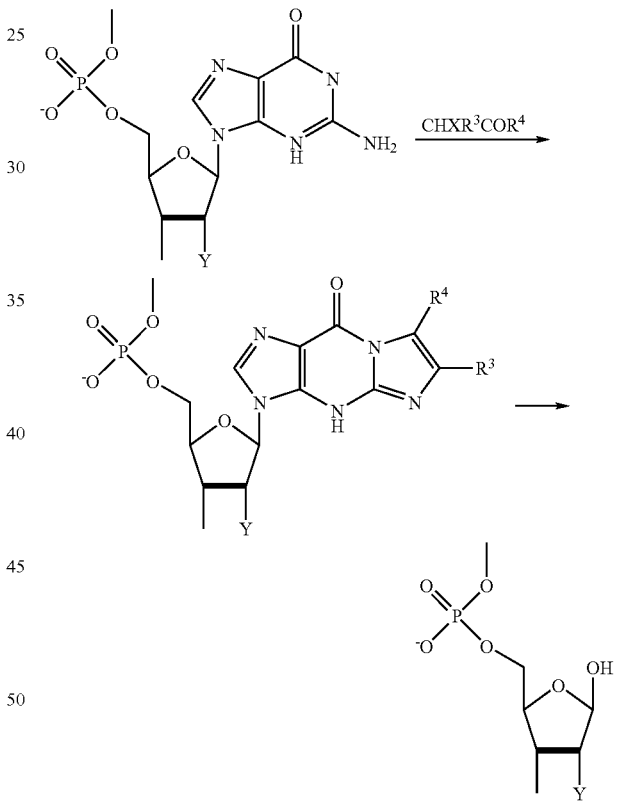

Figure 4:
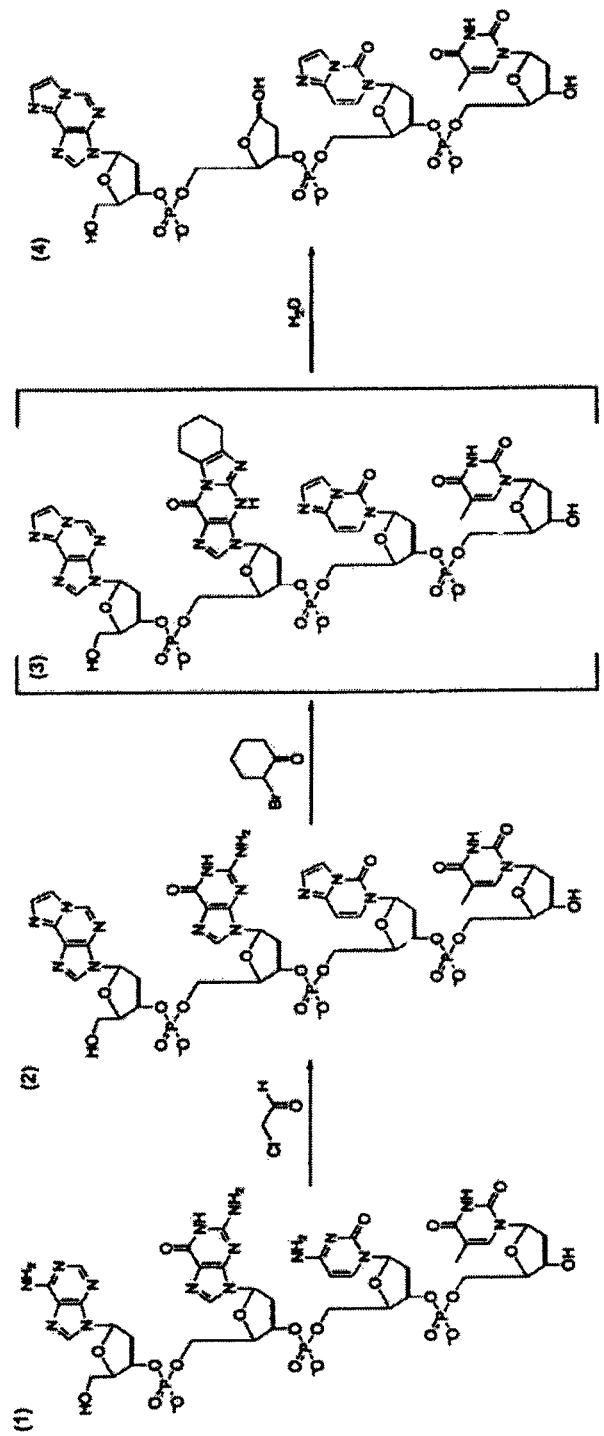
FIG. 4 is a view schematically depicting the reaction for modifying an oligonucleotide comprising the four essential nucleic acid bases in Example 1 in the second example group. The numerical figures represent the forms of the oligonucleotide at the individual steps; (1) represents the form before the reaction; (2) represents the form after the modification at the first step; (3) represents the form at an intermediate state of the modification at the second step; and (4) represents the form after the modification at the second step.

As the results of the modification reactions at such two steps, adenine (A) and cytosine (C) are modified. Guanine (G) is once modified, and the base is subsequently eliminated. Meanwhile, thymine (T) and uracil (U) are never modified. Consequently, the four bases in the polynucleotide are modified in such forms by which the modified bases can be discriminated from each other. As shown in FIG. 2 in the following Example, for example, a polynucleotide is modified as shown in FIGS. 4(3) and 4(4), so that the resulting bases are with different numbers of the rings composing the bases, while the bases still retain the sequence. Thus, the numbers of the rings can be detected by an appropriate means.

(Second Mode of the Enlargement Modification Method)

In the mode, a polynucleotide comprising adenine (A), guanine (G), cytosine (C) and thymine (T) or uracil (U) is modified at the following two-step reactions or three-step reactions.

First Step:
The same procedures as in the first mode of the enlargement modification method are carried out.

Second Step:
At the step, guanine (G) is modified as shown below in the chemical formula 13.

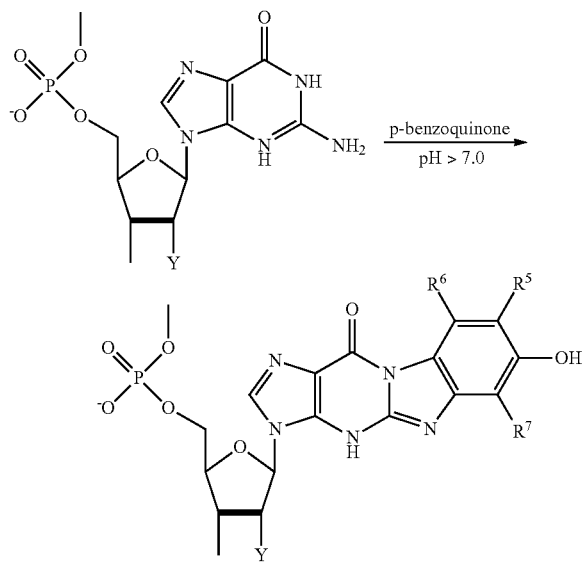

[Chemical formula 13]

In other words, the second mode of the enlargement modification method is a method for modifying nucleic acid bases, comprising allowing the bases to react with a p-benzoquinone derivative represented by the general formula below as the chemical formula 14.

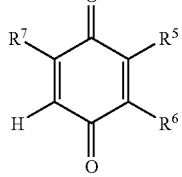

[Chemical formula 14]

In the chemical formula 14 as described above, $R^5$, $R^6$ and $R^7$ individually represent hydrogen atom or hydrocarbon groups, while the hydrocarbon groups include for example alkyl groups and aryl groups, preferably alkyl groups. The alkyl groups include for example linear alkyl groups with 18 or less carbon atoms, while the aryl groups include phenyl group. Additionally, $R^5$ and $R^6$ together may form a 5-membered or 6-membered ring. The 5-membered or 6-membered ring may satisfactorily be an aliphatic ring or aromatic ring.

The reactivity of the benzoquinone compound with the polynucleotide can be raised under controls of the conditions, so as to convert guanine (G) never modified at the first step to a benzoquinone adduct. Like the halogenated carbonyl compounds, the benzoquinone compound never reacts with thymine (T) or uracil (U).

The reaction conditions are as described below.

Reaction solvents: water, water-soluble organic solvents, or mixtures of water and water-soluble organic solvents. As the water-soluble organic solvents, methanol or ethanol, DMF, DMSO, dioxane, acetone, acetonitrile, dimethylcarbonate, ethylene carbonate, ethylene glycol, and diethylene glycol are preferable.

Polynucleotide concentration: 1 μM to 100 mM (particularly preferably a nucleic acid base concentration of 3.0 mM)

Concentration of the benzoquinone compound: 0.1 M to 2.0 M (particularly preferably 0.1 M)

pH: 7 to 9 (particularly preferably pH 7.2)

Reaction temperature: 0 to 65° C. (particularly preferably 50° C.)

Reaction time: 1 to 144 hours (particularly preferably 12 hours)

The pH adjustment is done, using various amines primarily including triethylamine, various buffers such as carboxylate buffers primarily including acetate buffer, formate buffer and phosphate buffer. Sodium acetate buffer is particularly preferable.

Figure 13:
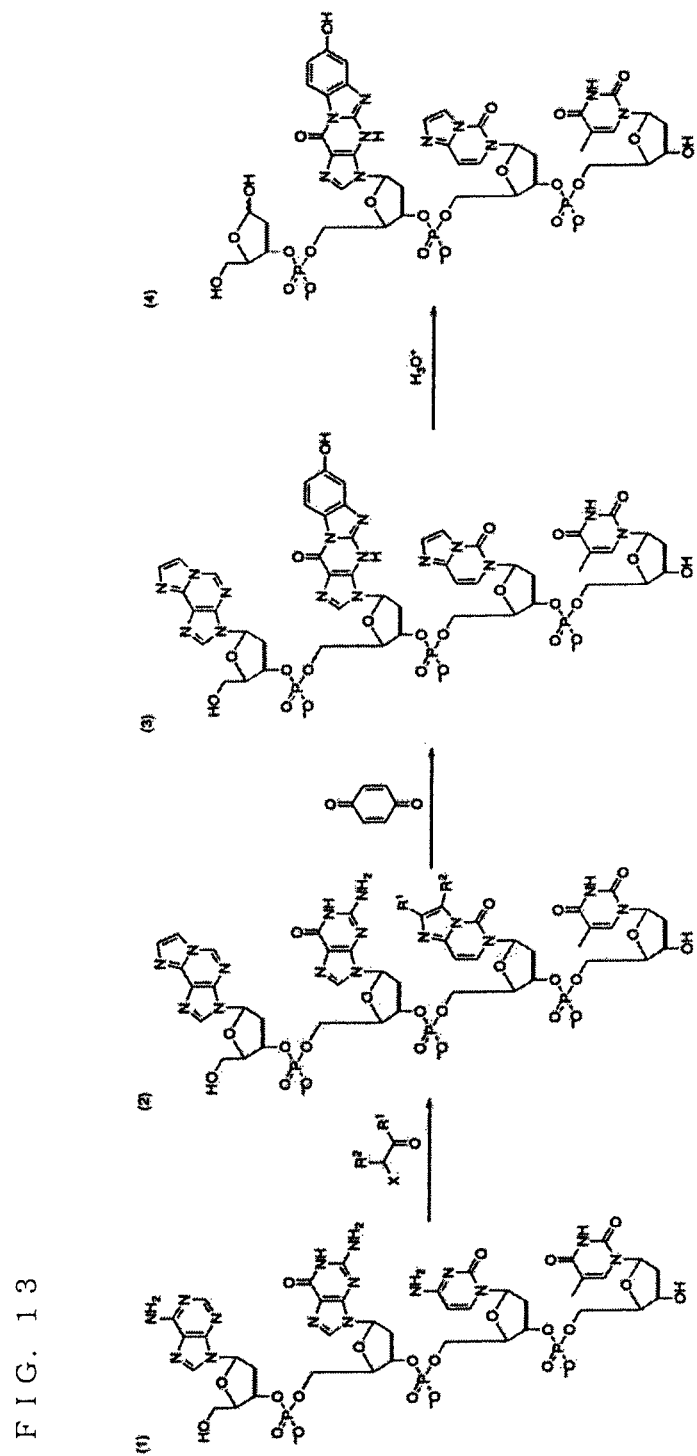
FIG. 13 is a view schematically showing the reaction for modifying an oligonucleotide comprising the four essential nucleic acid bases in the third example group. The numerical figures represent the forms of the oligonucleotide at the individual steps; (1) represents the form thereof before the reaction; (2) represents the form after the modification at the first step; (3) represents the form after the modification at the second step; and (4) represents the form after the modification at the third step.

As the results of the two-step modification reactions, adenine (A) and cytosine (C) are modified, while guanine (G) is modified in the different mode. Alternatively, thymine (T) and uracil (U) are never modified. Consequently, the four species of the bases in the polynucleotide can be modified in such a manner that the resulting modified bases can be discriminated from each other. In one Example described below, the polynucleotide is modified as shown in FIG. 13 (3), so that the numbers of the rings composing the base species differ from each other, while the sequence is retained. Thus, the numbers of the rings can be detected by an appropriate means.

Third Step:
Modified A is so relatively unstable that the base is selectively eliminated under acidic conditions (for example, pH 4 or less and the temperature of 37° C.) as shown below in the chemical formula 15.

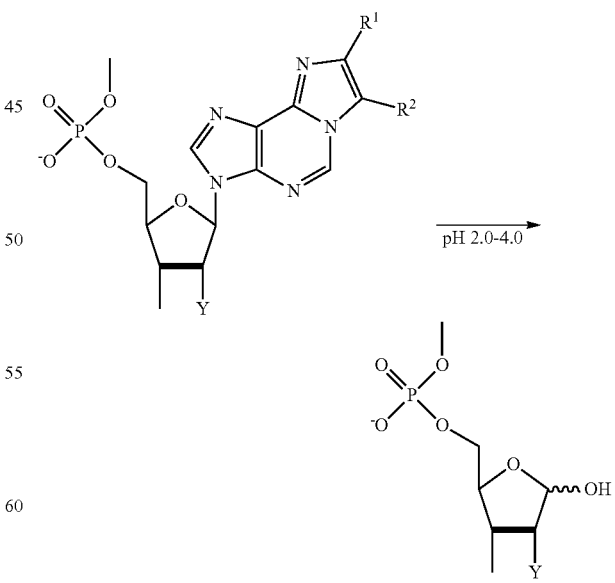

[Chemical formula 15]

Adenine (A) can be selectively eliminated via the modification reaction. Meanwhile, modified guanine (G) and modified cytosine (C) exist, while thymine (T) and uracil (U) are never modified. Consequently, the four bases in the polynucleotide are modified in such a manner that the modified bases can be discriminated from each other. As shown in FIG. 13(4) in the following Example, for example, a polynucleotide is modified, so that the resulting bases are with different numbers of the rings composing the bases while the bases still retain the sequence. Thus, the numbers of the rings can be detected by an appropriate means.

(Third Mode of the Enlargement Modification Method)

In the mode, a polynucleotide comprising adenine (A), guanine (G), cytosine (C) and thymine (T) or uracil (U) is modified by the following one-step or two-step reactions.

First Step:

At the step, adenine (A) and cytosine (C) are modified. In other words, the mode corresponds to a method for modifying nucleic acid bases, comprising a step of reaction with a benzoquinone compound shown above in the chemical formula 14.

At the step, the benzoquinone compound is allowed to react with a polynucleotide comprising adenine (A), guanine (G), cytosine (C) and thymine (T) or uracil (U). The length of the polynucleotide to be modified is a length of 2 to $3 \times 10^8$ base pairs, preferably 20 to 3,000 base pairs.

During the 24-hour reaction at pH 4.5, the benzoquinone derivative modifies adenine (A) and cytosine (C), but never modifies guanine (G), thymine (T) and uracil (U), as shown below in Table 1. The term "less than 0.1%" means the zone below detection limit.

TABLE 1

|  | Nucleoside | | | |
| --- | --- | --- | --- | --- |
|  | dA/rA | dC/rC | dG/rG | T/U |
| Conversion ratio (%) | >99% | >99% | <0.1% | <0.1% |

The reaction conditions are as described below.

Reaction solvents: water, water-soluble organic solvents, or mixtures of water and water-soluble organic solvents. As the water-soluble organic solvents, methanol or ethanol, DMF, DMSO, dioxane, acetone, acetonitrile, dimethylcarbonate, ethylene carbonate, ethylene glycol, and diethylene glycol are preferable.

Polynucleotide concentration: 1 μM to 100 mM (particularly preferably 2.0 mM on a nucleic acid base concentration basis)

Concentration of the benzoquinone compound: 0.1 M to 2.0 M (particularly preferably 60 mM)

pH: 4.5 to 6.5 (particularly preferably pH 4.5)

Reaction temperature: 20 to 45° C. (particularly preferably 37° C.)

Reaction time: 1 to 144 hours (particularly preferably 21 hours)

The pH adjustment is done, using various amines primarily including triethylamine, various buffers such as carboxylate buffers primarily including acetate buffer formate buffer and phosphate buffer. Sodium acetate buffer is particularly preferable.

Via the reaction, adenine (A) in the polynucleotide is modified as shown below in the chemical formula 16.

[Chemical formula 16]

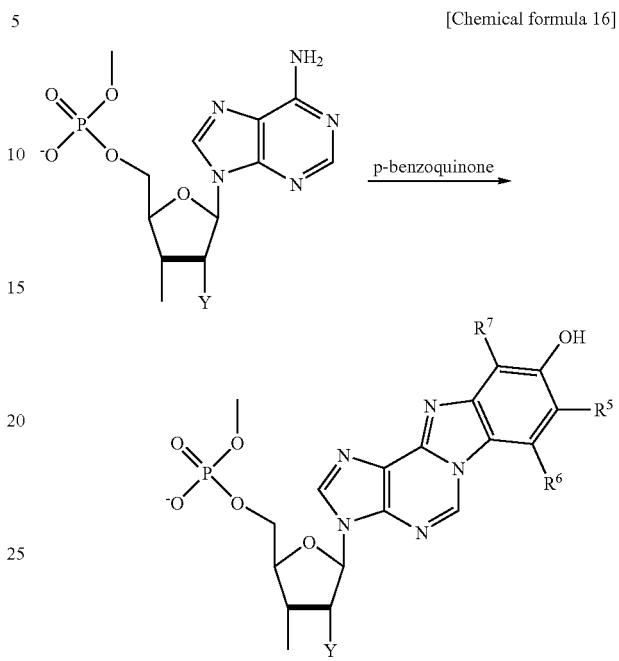

Additionally, cytosine (C) in the polynucleotide is modified as shown below in the chemical formula 17.

[Chemical formula 17]

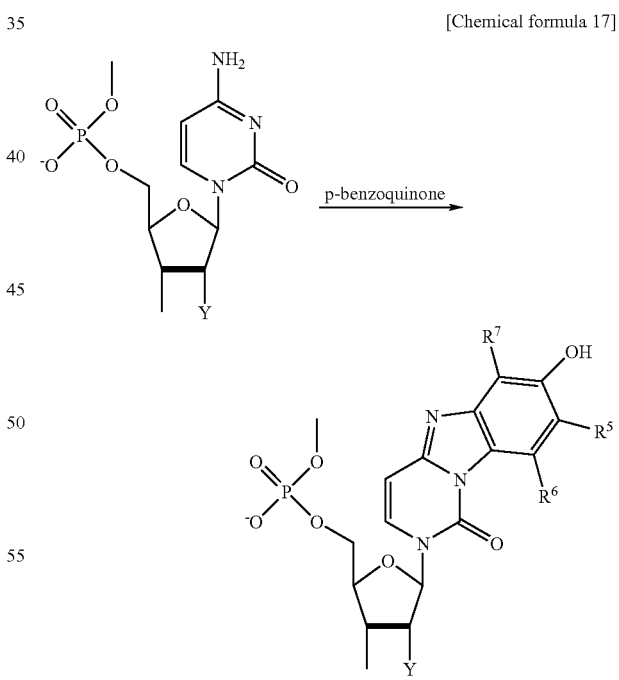

As the results of the modification reactions, adenine (A) and cytosine (C) are modified, while guanine (G), thymine (T) and uracil (U) are never modified. Consequently, the four species of the bases in the polynucleotide can be modified in such a manner that the resulting modified bases can be discriminated from each other. In one Example described below, the polynucleotide is modified as shown in FIGS. 13(3) and 13(4), so that the numbers of the rings composing the base species differ from each other, while the sequence is retained. Thus, the numbers of the rings can be detected by an appropriate means.

Second Step:

Via the reaction, adenine (A) and cytosine (C) in a polynucleotide are modified with the benzoquinone compound. Adenine among the modified bases is so relatively unstable that the base is eliminated under acidic conditions (for example, pH 4 or less and the temperature of 25° C.) as shown below in the chemical formula 18.

[Chemical formula 18]

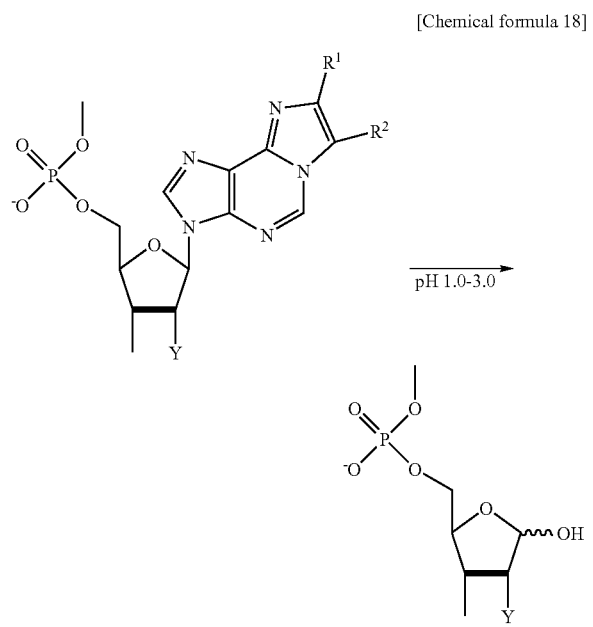

Figure 16:
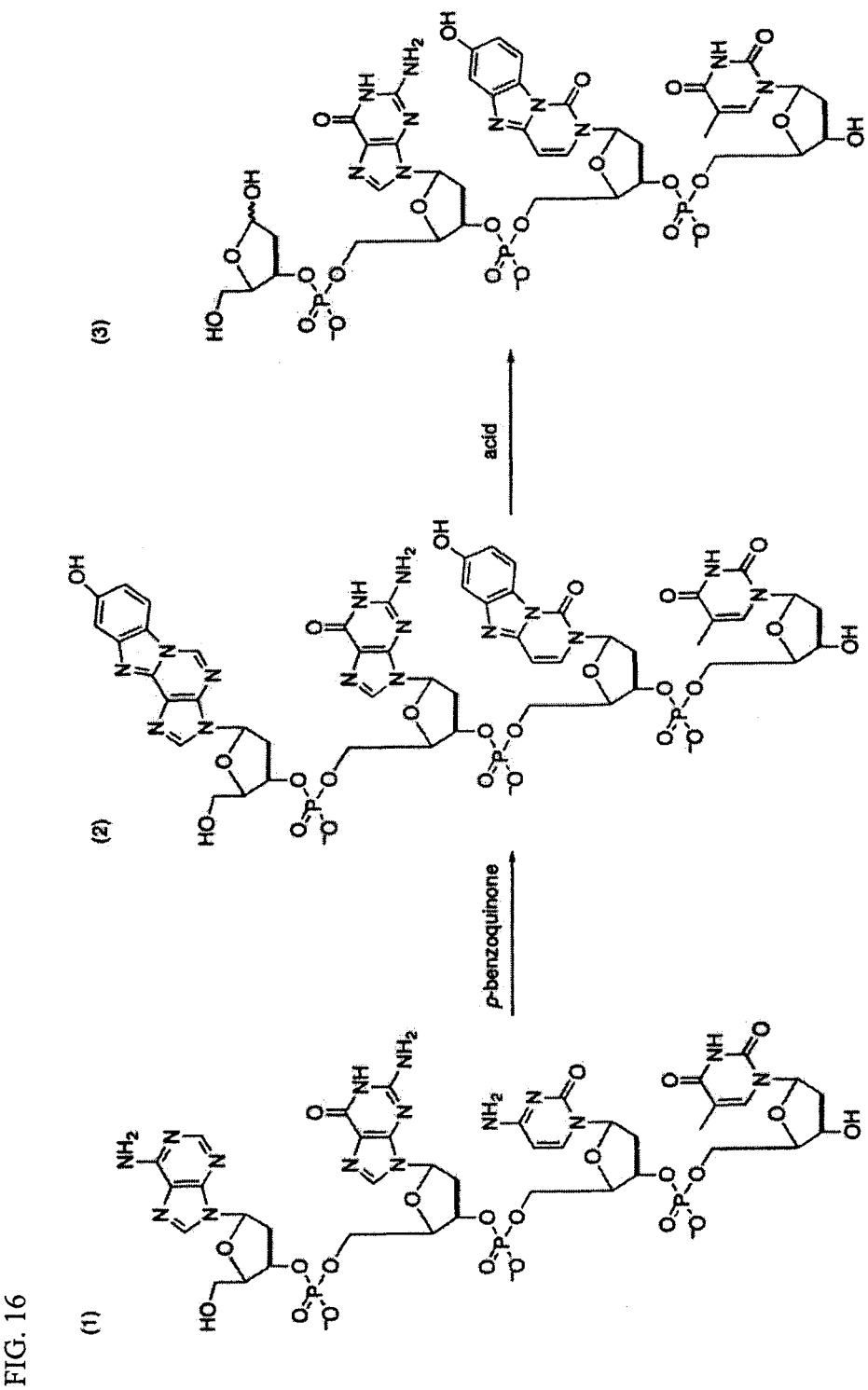
FIG. 16 is a view schematically showing the reaction for modifying an oligonucleotide comprising the four essential nucleic acid bases in the fourth example group. The numerical figures represent the forms of the oligonucleotide at the individual steps; (1) represents the form thereof before the reaction; (2) represents the form after the modification at the first step; and (3) represents the form after the modification at the second step.

As the results of the modification reactions at the one step or the two steps, adenine (A) is selectively eliminated, so that the four species of the bases in the polynucleotide can be modified in such a manner that the resulting modified bases can be discriminated from each other. In one Example described below as shown in FIG. 16, the polynucleotide is modified as shown in FIGS. 16(2) and 16(3), so that the numbers of the rings composing the base species differ from each other, while the sequence is retained. Thus, the numbers of the rings can be detected by an appropriate means. When the first step is done at pH 3.0 or less, a modified oligonucleotide is directly generated, from which the modified adenine has been released preliminarily.

EXAMPLES

The Examples of the invention are now described below. However, the technical scope of the invention is never limited by the following Examples.

First Example Group

First Substitution Modification Method

Example 1

Selective Release of Nucleic Acid Bases

For examining the release of the individual nucleic acid bases, first, 2'-deoxyadenosine (dA manufactured by YAMASA CORPORATION), 2'-deoxycytidine (dC manufactured by YAMASA CORPORATION), 2'-deoxyguanosine (dG manufactured by YAMASA CORPORATION), and thymidine (T manufactured by YAMASA CORPORATION) were used.

(1) Aqueous 0.03 M dA or dG solution to which about 30 equivalents of a cation exchange resin DOWEX 50WX8-200 ion exchange resin (H$^+$) were preliminarily added was then left to stand alone at ambient temperature for 2 hours, to assay the resulting 2'-deoxyribose. Based on the assay value, the recovery of the 2'-deoxyribose from dA or dG can be calculated. The recovery is considered as a conversion ratio of dA or dG to 2'-deoxyribose. As shown in Table 2, the recovery was a high recovery close to 100% in case of dA or dG. Because the released Ade and Gua were never assayed in the solutions, it is considered that these might have been adsorbed on the resin.

At a comparative test, dC and T were treated in the same manner with the cation exchange resin under the same conditions. It was confirmed that the released 2'-deoxyribose was at less than 1.0%. Since the recovery "less than 1.0%" is in the zone below detection limit, it is considered that by the method (1), absolutely no base release occurred regarding dC and T. The same results are obtained when the solution is left to stand in a 1.0 M hydrochloric acid solution (nucleoside concentration at 0.03 M) at ambient temperature for 24 hours.

Thus, it is understood that the method (1) is substantially effective as a means for selectively releasing the purine bases.

(2) Aqueous 0.13 M dC or T solution to which hydrazine was preliminarily added (7.9 M) was then left to stand alone at ambient temperature for time periods in hour as shown in Table 2. Then, the resulting solution was treated with the same cation exchange resin used above in (1). The cation exchange resin in this case was used for capturing the decomposed and released bases, so the cation exchange resin never composes the means for selectively releasing any bases. Via the treatment described above, 2'-deoxyribose generated was assayed in the same manner as described above in (1), to calculate the recovery. As shown in Table 2, Cyt and Thy were individually released at extremely high ratios close to 100%, to quantitatively generate 2'-deoxyribose. Cyt and Thy were released while involving the decomposition reaction called hydrazine decomposition. Because no decomposition products were observed in the reaction solution, it is considered that the decomposition products might have been adsorbed on the resin.

At a comparative test, dA and dG were treated for the hydrazine decomposition in the same manner, to assay the generated 2'-deoxyribose. It was confirmed that the released 2'-deoxyribose was at a value less than 1.0% in the zone below detection limit.

Therefore, the method (2) is substantially effective as a means for selectively releasing pyrimidine bases.

TABLE 2

| base (conc.) | reagent (conc.) | Time (h) | yield (%) |
|---|---|---|---|
| dA (0.03 M) | DOWEX 50WX8-200 ion-exchange resin (H+) | 24 | 98-96 |
| dG (0.03 M) | DOWEX 50WX8-200 ion-exchange resin (H+) | 24 | 98-96 |
| dC•HCl (0.03 M) | DOWEX 50WX8-200 ion-exchange resin (H+) | 24 | <1.0 |
| T (0.03 M) | DOWEX 50WX8-200 ion-exchange resin (H+) | 24 | <1.0 |
| dA (0.03 M) | hydrazine (7.9 M) | 5 | <1.0 |
| dG (0.03 M) | hydrazine (7.9 M) | 5 | <1.0 |

TABLE 2-continued

| base (conc.) | reagent (conc.) | Time (h) | yield (%) |
|---|---|---|---|
| dC·HCl (0.03 M) | hydrazine (7.9 M) | 5 | 98 |
| T (0.03 M) | hydrazine (7.9 M) | 5 | 95 |

(3) After dimethylsulfuric acid (10 mM) was added to individual aqueous 1.0 M dimethylsulfate buffer solutions of dA and dG and the resulting solutions were left to stand alone for 24 hours, the generated 2'-deoxyribose was assayed in the same manner as described above in (1). As shown in Table 3, Gua is eliminated more preferentially than Ade.

At a comparative test, dC and T were treated in the same manner under the same conditions. It was confirmed that the released 2'-deoxyribose had a recovery of less than 1.0% which was detection unit. Since the recovery "less than 1.0%" is in the zone below detection limit, it is considered that by the method (3), absolutely no base release occurred regarding dC and T. The same results are obtained when the solutions are left to stand alone in a 1.0 M hydrochloric acid solution (nucleoside concentration at 0.03 M) at ambient temperature for 24 hours.

(4) Aqueous 0.13 M dC- and T solutions to which hydrazine (7.9 M) and NaCl (0.1 M) were preliminarily added were then left to stand alone at ambient temperature for 24 hours, and then, the resulting solutions were treated with the same cation exchange resin used above in (1). The cation exchange resin in this case was used for capturing the decomposed and released bases and unreactive nucleosides, so the cation exchange resin never composes the means for selectively releasing bases. Via the treatment described above, 2'-deoxyriboses generated were assayed in the same manner as described above in (1), to calculate the recovery. As shown in Table 3, it was confirmed that Cyt was released more preferentially than Thy. Involving the decomposition reaction called hydrazine decomposition, Cyt and Thy were released. By the NaCl addition, the progress of the Thy decomposition with hydrazine was inhibited. Because T and Thy were never adsorbed on the resin, the recovery of not 2'-deoxyribose but T was defined as conversion ratio in the system.

At a comparative test, dA and dG were treated for the hydrazine decomposition under the same conditions, to assay the generated 2'-deoxyribose. It was confirmed that the released 2'-deoxyribose was at a value less than 1.0% in the zone below detection limit.

Therefore, the method (2) is substantially effective as a means for selectively releasing the base cytosine.

TABLE 3

| Reaction agent | dA | dC | dG | T |
|---|---|---|---|---|
| 0.1 M (CH$_3$)$_2$SO$_4$ | ~10% | <0.1% | >99% | <0.1% |
| 7.9 M N$_2$H$_4$ + 1.0 M NaCl | <0.1% | >99% | <0.1% | ~10% |

Example 2

Incorporation of Substituent into the Site of the Nucleic Acid Base Having been Bound The incorporation of a substituent via reducing amination into the 2'-deoxyribose generated from the release of a nucleic acid base was examined.

When sodium cyanoborohydride (0.5 M, manufactured by Tokyo Chemical Industry Co., Ltd.) was added to a 2'-deoxyribose solution in a solvent and acetic acid (1:2, 0.05 M) and was then left to stand alone at ambient temperature for 2 hours, the corresponding secondary amine was generated at a high reaction efficiency, as verified by TLC. Several types of solvents instead of the solvent described above were also examined, and a high reaction efficiency was retained with any of the solvents. These results are shown below in Table 4.

TABLE 4

| amine (conc.) | reductant (conc.) | solvent | temp (°C.) | time (h) | yield (%) |
|---|---|---|---|---|---|
| ethanolamine (0.05 M) | NaCNBH$_3$ (0.5 M) | CH$_3$COOH: DMF = 1:2 | 25 | 2 | 90 |
| 2-aminomethyl-pyrene (0.05 M) | NaCNBH$_3$ (0.5 M) | CH$_3$COOH: DMF = 1:2 | 25 | 3 | 85 |
| 2-aminomethyl-pyrene (0.05 M) | Ph$_2$SiH$_2$ (0.5 M) | CF$_3$COOH: CE$_3$CN = 1:5 | 25 | 1 | 75 |
| 2-aminomethyl-pyrene (0.05 M) | HCOOH (0.5 M), [Rh(C$_5$H$_5$)Cl$_2$]$_2$ (0.001 M), | DMF | 72 | 0.5 | 95 |
| 2-aminomethyl-pyrene (0.05 M) | HCOOH (0.5 M), [Rh(cod)Cl$_2$]$_2$ (0.001 M), | DMF | 72 | 0.5 | 95 |

Evaluation of Examples 1 and 2

Examples 1 and 2 were carried out at nucleoside levels. It is verified that in Example 3 below, these means are also sufficiently effective for oligonucleotides and long-chain nucleic acids. At this time point, methods for selectively releasing purine bases (Ade and Gua) and pyrimidine bases (Cyt and Thy) have been achieved. By further examining the conditions, the four bases may selectively be released.

By appropriately selecting an amine to be modified, a substituent with a structure and properties significantly different depending on the base may be incorporated. In other words, the process of the nucleic acid base-selective substitution modification method is repeatedly carried out for every species of plural bases in a nucleic acid, where labeling compounds of different types depending on every base species by which the bases can be discriminated from each other can be incorporated.

Example 3

Substitution and Modification of Nucleic Acid Bases in Oligonucleotide

In the Example, the substitution modification method of nucleic acid bases was applied to an oligonucleotide. For observation with a transmission electron microscope (TEM), amino-terminal undecagold (amino-terminal UG) giving sufficient contrast under TEM observation was used as the amine for use in the substitution.

The scheme for releasing adenine from the oligonucleotide and then incorporating the metal cluster label namely amino-terminal UG in the site to which adenine has been bound is as described above in "the chemical formula 9".

As shown in the chemical formula 9, MilliQ water (10 µL) and DOWEX-50WX8-200 ion exchange resin (1 mg) were added to dA$_{20}$ (00.1 µM, 3 µl, 0.03×10$^{-7}$ pmol, manufactured by Invitrogen), and the resulting mixture was left to stand at ambient temperature for 2 hours. 10 µL of the supernatant was taken out, and diluted to 10,000 fold. The diluted solution was transferred in a 1.5-ml Eppendorf tube. The amino-terminal UG (1.2 nmol, manufactured by Nanoprobe Corporation) and NaCNBH$_3$ (8.2 mg) were diluted with CH$_3$COOH (80 µL)

and MilliQ water (180 μL), and the resulting diluted solution was mixed with the diluted solution described above, which was then left to stand at ambient temperature for 2 hours for observation with TEM (EM-1200EX of positive mode, manufactured by JEOL Ltd.), to obtain the TEM image shown in FIG. 1. The size bar shown in the bottom of FIG. 1 shows "50 nm". Because the diameter (2.1 nm) of UG is significantly larger than the base distance (0.75 nm), not all the bases were substituted. However, it was shown that many Ade species were substituted with UG.

Under the same conditions, $dk_{20-100}$ (0.1 μM, 3 μl, 0.03× $10^{-7}$ pmol, manufactured by Invitrogen) was treated. The TEM image shown in FIG. 2 was obtained under observation with TEM (EM-2200 of scanning TEM, negative mode, manufactured by JEOL Ltd.). The size bar shown in the bottom of FIG. 2 shows "20 nm".

An aqueous 1 M HCl solution (3.5 μL) was added to $dAT_9AT_8A$ (188 μM, 354 μL, 66.7 nmol, manufactured by Gene Design Inc.), which was then left to stand alone at 55° C. for 14 hours. 50 μL was taken out and applied to a gel filtration column (MicroSpin G-25 manufactured by GE HEALTH CARE), and the resulting filtrate was freeze-dried. The residue was dissolved in 282 mL of dried DMF. A DMF solution of amino-terminal UG (200 μM, 10 μL, 2.0 nmol, manufactured by Nanoprobe Corporation) and a DMF solution of $NaCNBH_3$ (2.0 M, 10 μL, 20 μmol, manufactured by TCI) were mixed with $CH_3COOH$ (10 μL). The resulting mixture was then left to stand alone at ambient temperature for 2 hours, for observation with TEM (EM-2200 manufactured by JEOL Ltd., scanning TEM, negative mode), to obtain the TEM image shown in FIG. 3. The size bar shown in the bottom of FIG. 3 is "10 nm". The three points with strong signals were derived from UG and individually corresponded to the position A. As estimated, the distance between the individual points was about 10 nm, which indicates that all of the A in $dAT_9AT_8A$ were substituted with UG.

Example 1

Modification of dAGCT

In the following Example, HPLC analysis was done with the following apparatuses under the following conditions.
Low-pressure gradient pump: PU-2089 Plus manufactured by JASCO Corporation
Sampling unit: AS-950-10
Multi-wave UV detector: MD-2015 Plus
Column oven: 860-CO manufactured by JASCO Corporation
Column: COSMOSIL 5C18-ARII manufactured by Nakarai Tesque
Eluent: 0.1 M TEAA buffer (pH 7.0)/$CH_3CN$ ($CH_3CN$ 3%→30%, 30 minutes)
Elution velocity: 0.5 mL/min
Temperature for Analysis: 40° C.
UV wavelength for detection: 254 nm
Further, mass spectrometry was done with the following apparatuses under the following conditions.
Mass spectrometric apparatus of ion spray type and quintuplet-fly-time measurement type: Q-T of Premier manufactured by Micromass
Direct Injection
Negative mode
Capillary voltage: 2.6 kV
Corn voltage: 60 V
Collision energy: 4 eV measured by MS
Ion source temperature: 100° C.
Desolvation temperature: 250° C.
Desolvation gas: 750 L/hr Synthetic Example 1

200 mL of ethyl acetate was placed in a 300-mL Erlenmeyer flask, to which cyclohexanone (manufactured by Sigma Aldrich, GC purity of 99.8%, 2.1 mL, 20 mmol) and N-bromosuccinimide (manufactured by Wako Pure Chemical Co., Ltd., a titration purity of 98% or more, 3.9 g, 22 mmol) were added for dissolution. Then, Amberlyst-15 (R) (catalyst manufactured by Sigma Aldrich, dry product, 15 g) was added to the resulting solution, for agitation at ambient temperature for 35 minutes. By filtering the solution, Amberlyst-15 (R) was removed. The resulting filtrate was dried and concentrated over sodium sulfate, and was then purified using a medium-pressure separation and purification apparatus (Purif compact manufactured by Moritec Corporation, column: Purif-Pack manufactured by Moritec Corporation, 15 μm silica gel of 30 g), to obtain 2-bromocyclohexanone.

The medium-pressure separation conditions were as follows.
Eluent: hexane/ethyl acetate (ethyl acetate 0%→25%, 20 minutes)
Elution velocity: 20 mL/min
UV wavelength for detection: 254 nm
The structure of the generated 2-bromocyclohexanone was verified by NMR.
$^1$H NMR (500 MHz, $CDCl_3$): σ 1.69-2.03 (m, 3H), 2.17-2.34 (m, 3H), 2.93-2.99 (m, 2H), 4.40-4.43 (m, 1H).

Reaction Example 1

Figure 5:
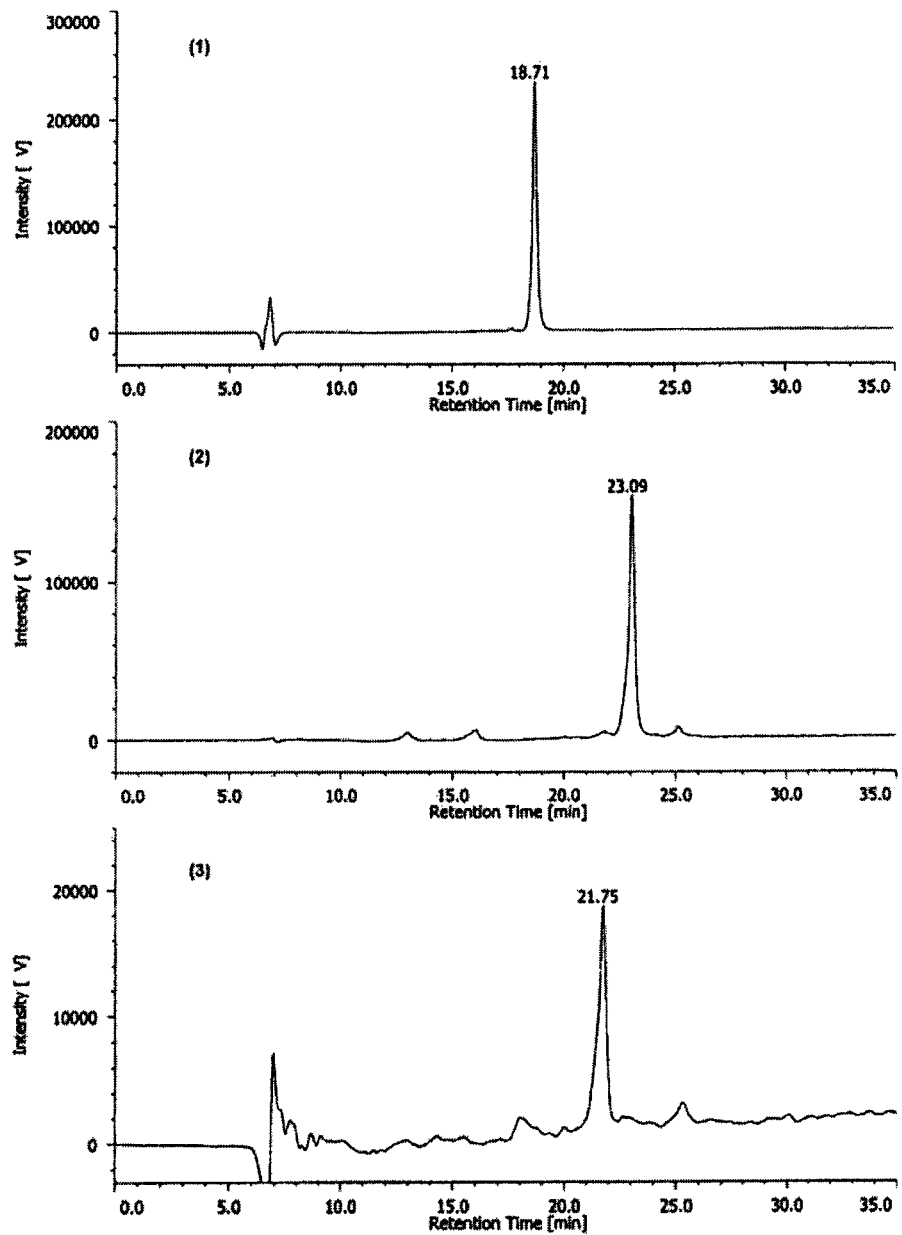
FIG. 5 shows HPLC charts of the oligonucleotide obtained in Example 1 in the second example group. The numerical figures (1) to (3) in the charts represent steps; (1) represents the HPLC chart before the reaction; (2) represents the HPLC chart after the modification at the first step; and (3) represents the HPLC chart after the modification at the second step.

An oligonucleotide comprising all of the four essential nucleic acid bases (FIG. 4(1)), namely dAGCT manufactured by Gene Design Inc. was prepared. The HPLC purity was 85% or more (A260 nm) (FIG. 5(1)).
(First Step)
A mixture of an aqueous solution of the oligonucleotide (0.11 mM, 4.4 mL, 0.50 μmol) and chloroacetaldehyde (manufactured by Tokyo Chemical Industry Co., Ltd., aqueous 40% solution, 6.49 mL, 40 μmol) was transferred in a 30-ml Erlenmeyer flask, to which methanol was added to a final total volume of 20 mL (methanol:water=1:1 finally). After the pH was adjusted to pH 5.0 using triethylamine (the GC purity of 99% or more, manufactured by Kishida Chemical Industry Co., Ltd.), the mixture was treated at 37° C. for 24 hours. Methylene chloride (40 mL) was added to the reaction solution transferred into a separation funnel, which was then left to stand alone for 30 minutes to remove the resulting organic layer. A series of the above procedures were carried out three times, and the resulting aqueous layer was concentrated and dried, to obtain the intended labeled tetramer (FIG. 4(2)).

Figure 6:
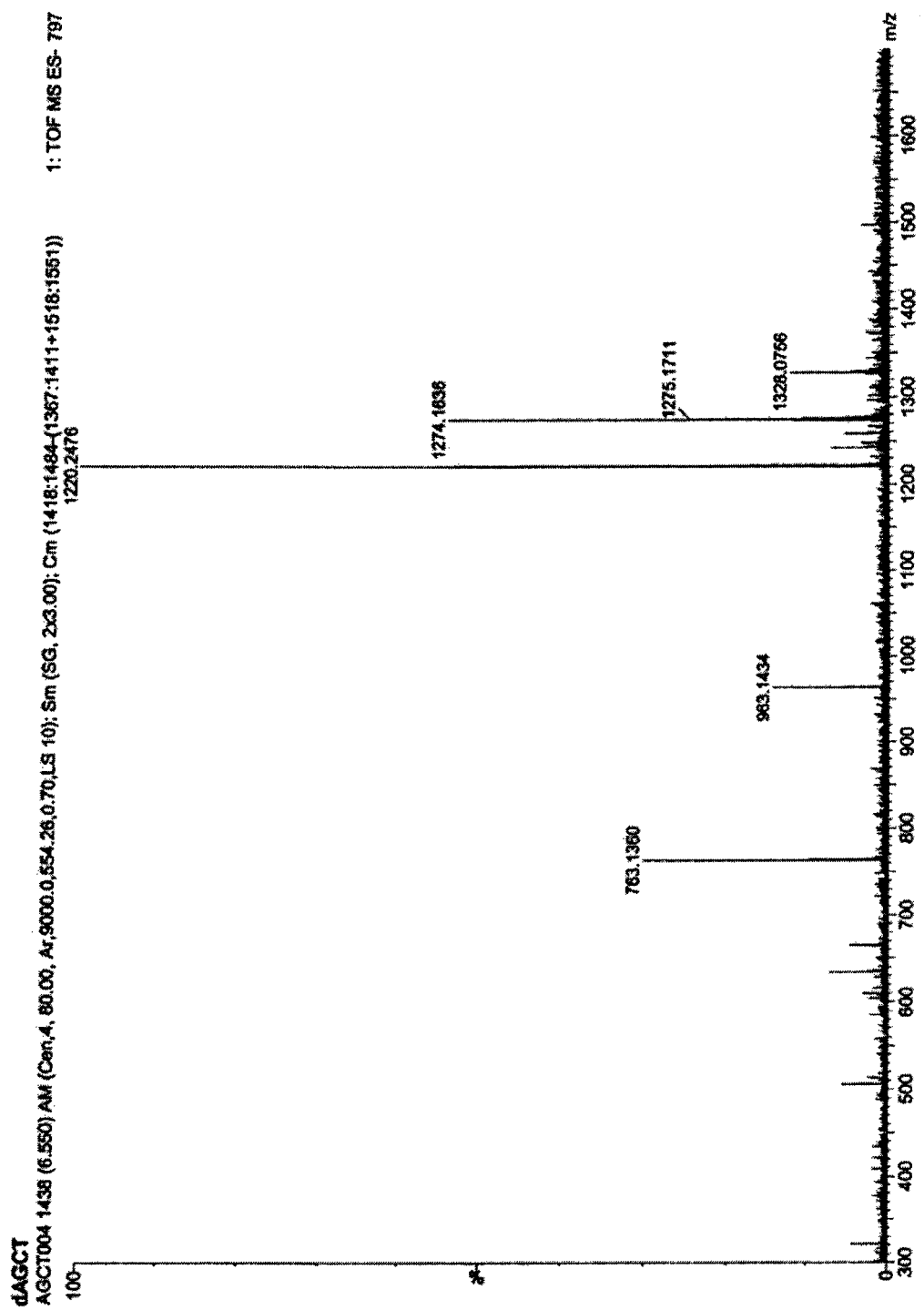
FIG. 6 shows the mass spectrum of the oligonucleotide after the modification at the first step in Example 1 in the second example group.

The mass spectrum of the resulting product is shown in FIG. 6. By the mass spectrometry, a main peak was observed at m/z 1220.2 (M−1) close to the calculated value (calculated for $C_{43}H_{49}N_{15}O_{22}P_3$) (M−1): m/z 1220.2, verifying the structure of the chemical formula 2.
(Second Step)
The modified oligonucleotide obtained above was dissolved again in distilled water (0.1 mM, 0.50 mL, 0.21 μmol); 10 mL of the resulting solution was transferred into a sample bottle, to which an aqueous methanol solution (1.6 mL, finally methanol:water=2:1) of 2-bromocyclohexanone obtained in the Synthetic Example 1 (NMR purity of 95%, 0.49 mL, 4.1 mmol) is added, to obtain a final total volume of 2.1 mL. After the solution was adjusted to pH 5.0, using acetic acid, the solution was treated at 37° C. for 24 hours. Methylene chloride (3.1 mL) was added to the solution, which was then left to stand alone for 30 minutes to remove the resulting organic layer. A series of the above procedures were carried out three times, and the resulting aqueous layer was concentrated and dried, to obtain the intended labeled tetramer (FIG. 4(4)).

Figure 7:
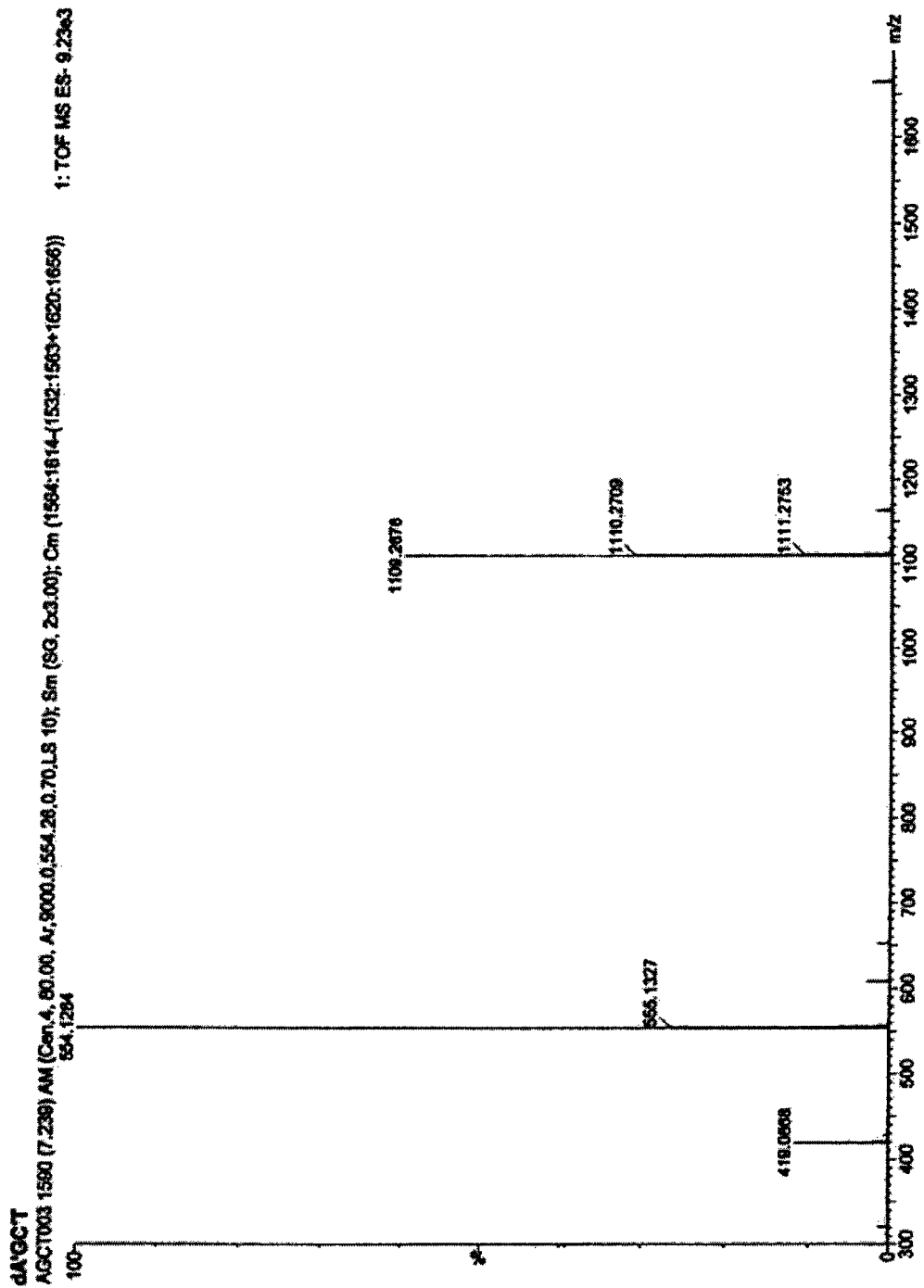
FIG. 7 shows the mass spectrum of the oligonucleotide after the modification at the second step in Example 1 in the second example group.

The mass spectrum of the resulting product is shown in FIG. 7. By the mass spectrometry, a main peak was observed at m/z 1109.3 (M−1) close to the calculated value [calculated for $(C_{38}H_{46}N_{10}O_{22}P_3Na)$ (M−1): m/z 1110.2].

Based on the structure (FIG. 4(4)), it is deduced that that guanine (G) once reacts with 2-bromocyclohexanone and falls into a modified form as a reaction intermediate (FIG. 4(3)).

Example 2

Modification of dAAATATTAATATTAATATTT

In the following Example, HPLC analysis was done under the following conditions.

Low-pressure gradient unit: LG-1580-02 manufactured by JASCO Corporation

Pump: PU-980 manufactured by JASCO Corporation

Sampling unit: AS-950-10 manufactured by JASCO Corporation

CD-UV detector: CD-1595 manufactured by JASCO Corporation

Column oven: 860-CO manufactured by JASCO Corporation

Column: COSMOSIL 5C18-ARII manufactured by Nakarai Tesque

Eluent: 0.1M TEAA buffer (pH 7.0)/$CH_3CN$ ($CH_3CN$ 8%→30%, 30 minutes)

Elution velocity: 0.5 mL/min

Temperature for Analysis: 40° C.

UV wavelength for detection: 254 nm

Further, mass spectrometry was done under the following conditions.

Apparatus: REFLEX III manufactured by Bruker Daltonics

Ionization type: matrix-assisted laser excitation ionization method (MALDI)

Detection method: fly-time measurement

Laser species: $N_2$ laser

Measurement method: linear

Matrix: 3-hydroxypicolinic acid

Detection mode: negative.

Figure 8:
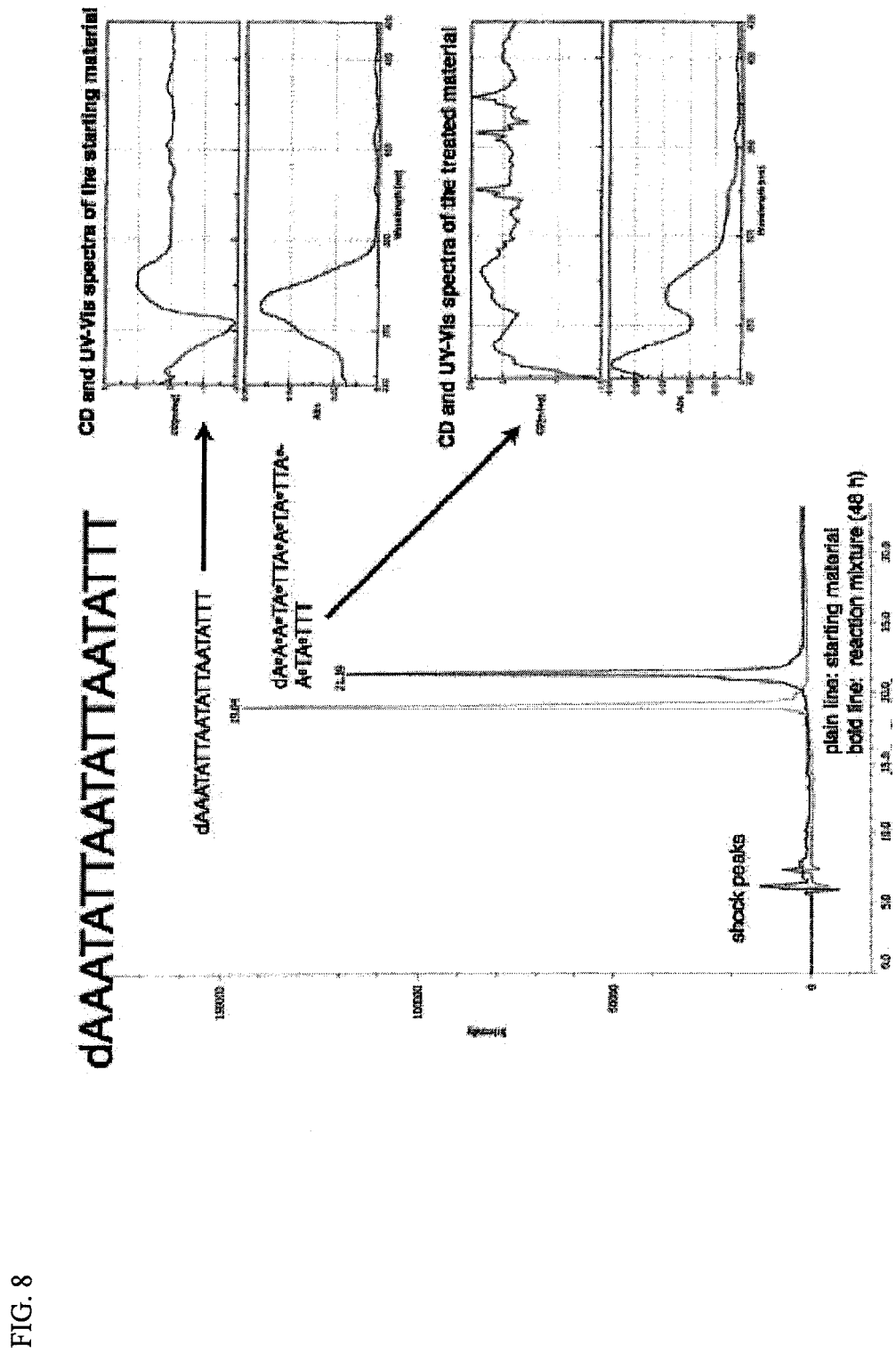
FIG. 8 shows the HPLC charts of the raw material in Example 2 in the second example group and the oligonucleotide after the modification, the absorption spectra thereof (UV-Vis) and the circular dichromatic dispersion spectra (CD) thereof.

The inventors added an aqueous chloroacetaldehyde solution (2.0 M, manufactured by Tokyo Chemical Industry Co., Ltd.) at the same volume as that of an aqueous solution (0.1 mM) of a 20-mer of deoxyribonucleotides, ie. dAAATATTAATATTAATATTT forming a double strand by itself, to the aqueous solution. Then, the resulting solution was adjusted to pH 5.0, using triethylamine, for treatment at 37° C. for 48 hours. After methylene chloride (at a volume two-fold that of the reaction solution) was added, the organic phase was removed. The procedure was repeated twice, and FIG. 8 shows an HPLC chart of the resulting reaction solution. The thin line shows the HPLC chart of the raw material, while the broad line shows the HPLC chart of the reaction solution. In FIG. 8, these charts are overlaid together and are shown. FIG. 8 shows peak transfer and the appearance of novel absorption on the absorption spectrum, indicating that the raw material oligonucleotide was modified. By the mass spectrometry, a main peak was observed at m/z 6352.4 (M−1) close to the calculated value [calculated for $(C_{120}H_{251}N_{70}O_{118}P_{19})$ (M−1): m/z 6352.3], indicating that all of the ten adenine species (A) contained in the raw material were modified.

Discussion about Handling of Double-Stranded Nucleic Acid

Since nucleic acid as an analytical subject forms a double strand based on the formation of complimentary base pairs or forms a high-order configuration within the molecule, a completely single-stranded structure not forming the intermolecular high-order configuration for is needed for obtaining sequence information. Therefore, generally, a large volume of dissociation agents and the like are used. However, it is not yet satisfactory. Nucleic acid fragments of long chains, or a certain type of sequences readily forming intermolecular multi-order configurations are still problematic. In accordance with the invention, one of bases forming each of two sets of complimentary base pairs namely adenine-thymine base pair (Ade-Thy) and guanine-cytosine base pair (Gua-Cyt) is Ade or Cyt, which is modified with the halogenated carbonyl compound or the benzoquinone compound; otherwise, Ade, Cyt and Gua are modified with the halogenated carbonyl compound or the benzoquinone compound, so that these bases are converted to structures never forming any base pair. Hence, the resulting modified nucleic acid cannot form any double stand or a high-order intermolecular configuration, as based on base pair formation, so that the modified nucleic acid of the invention exists at a completely single-stranded state, which is a state very readily treatable with various measurement apparatuses for the purpose of obtaining sequence information. It is indicated that the invention makes great contributions to the amplification of the difference in the individual nucleic acid bases and also makes great contributions to the formation of a completely single-stranded nucleic acid. As show in FIG. 8, the phenomenon is supported by the finding that the wave form via the positive and negative inversion (Cotton effect) representing the formation of a double stand, as observed for the raw material forming a double strand by circular dichroism spectroscopy, is never observed for the modified oligonucleotide.

Example 3

Modification of $dAC_{14}AC_9AC_4ACAC$

In the following Example, HPLC analysis was done under the following conditions.

Low-pressure gradient unit: LG-1580-02 manufactured by JASCO Corporation

Pump: PU-980 manufactured by JASCO Corporation

Sampling unit: AS-950-10 manufactured by JASCO Corporation

CD-UV detector: CD-1595 manufactured by JASCO Corporation

Column oven: 860-CO manufactured by JASCO Corporation

Column: COSMOSIL 5C18-ARII manufactured by Nakarai Tesque

Eluent: 0.1M TEAA buffer (pH 7.0)/$CH_3CN$ ($CH_3CN$ 8%→30%, 30 minutes)

Elution velocity: 0.5 mL/min

Temperature for Analysis: 40° C.

UV wavelength for detection: 254 nm

Further, mass spectrometry was done under the following conditions.

Apparatus: REFLEX III manufactured by Bruker Daltonics

Ionization type: matrix-assisted laser excitation ionization method (MALDI)

Detection method: fly-time measurement

Laser species: $N_2$ laser

Measurement method: linear

Matrix: 3-hydroxypicolinic acid

Detection mode: negative.

Figure 9:
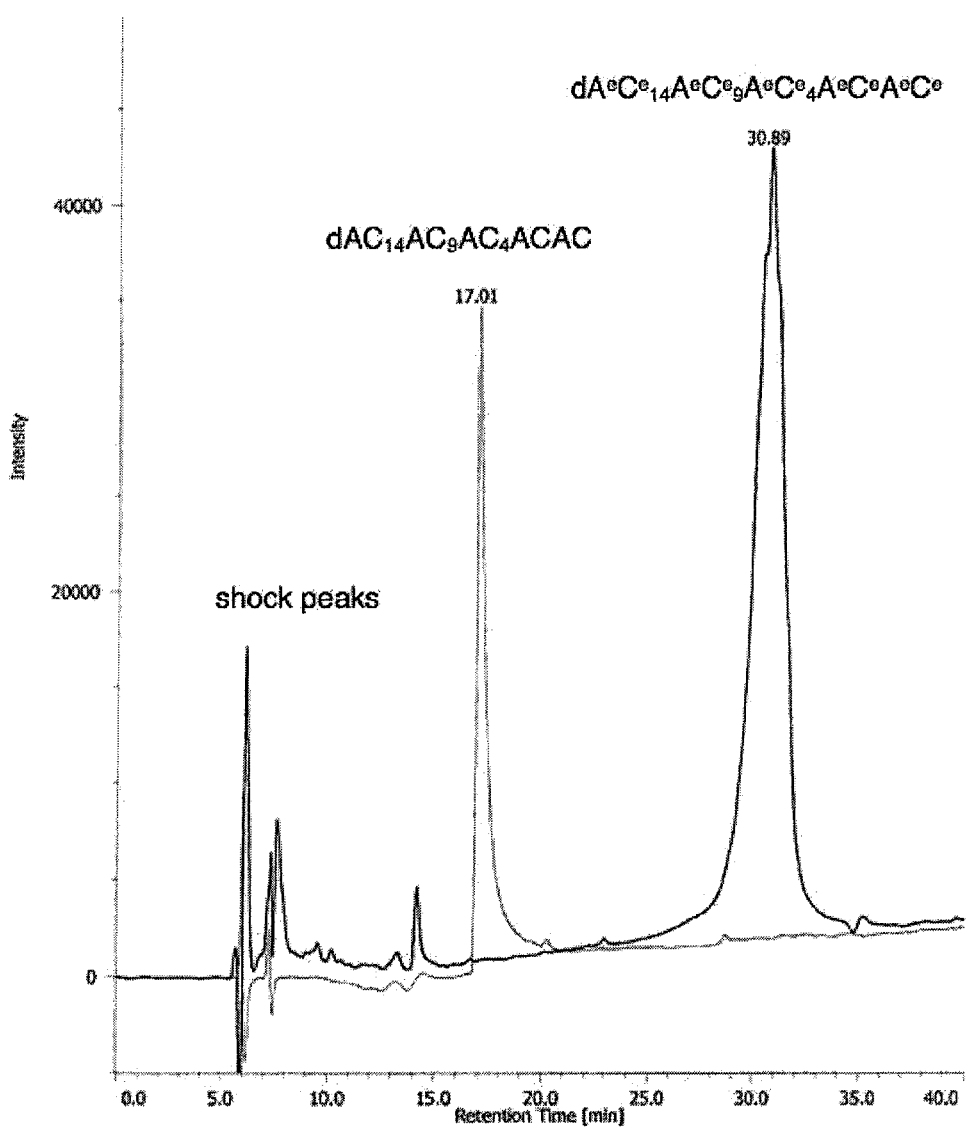
FIG. 9 shows the HPLC charts of the raw material in Example 3 in the second example group and the oligonucleotide after the modification.

The inventors added an aqueous chloroacetaldehyde solution (2.0 M manufactured by Tokyo Chemical Industry Co., Ltd.) at the same volume as that of an aqueous solution (0.1 mM) of $dAC_{14}AC_9AC_4ACAC$ of which all the nucleic acid bases were subjects for such modification, to the aqueous solution. Then, the resulting solution was adjusted to pH 5.0, using triethylamine, for treatment at 37° C. for 48 hours. After methylene chloride (at a volume two-fold that of the reaction solution) was added, the organic phase was removed. The procedure was repeated twice, and FIG. 9 shows an HPLC chart of the resulting reaction solution. A peak transfer was verified, indicating the generation of an oligonucleotide where adenine (A) and cytosine (C) in total of 34 as contained in the raw material oligonucleotide were modified to etheno bases, namely $Ade^e$ and $Cyt^e$. Additionally, a main peak was observed at m/z 10707.1 (M−1) close to the calculated value [calculated for $(C_{379}H_{525}N_{112}O_{197}P_{33})$ (M−1): m/z 10707.3].

Discussion about Successive Modification of Bases

It was verified that in accordance with the invention relating to the chemical modification of nucleic acid, all bases in a nucleic acid could be modified with no problem, even when the bases as subjects for the modification successively exist. In the Example, only the oligonucleotides of which the modification can be verified by mass spectrometry are shown. However, the Example shows that the invention is applicable practically to a nucleic acid of any length or any sequence. Thus, the modification in accordance with the invention is an essential phenomenon.

Example 4

Modification of Salmon Sperm DNA

In the following Example, HPLC analysis was done under the following conditions.

Low-pressure gradient pump: PU-2089 Plus manufactured by JASCO Corporation

Sampling unit: AS-950-10

Multi-wavelength UV detector: MD-2015 Plus

Column oven: 860-CO manufactured by JASCO Corporation

Column: COSMOSIL 5C18-ARII manufactured by Nakarai Tesque

Eluent: 0.1 M TEAA buffer (pH 7.0)/$CH_3CN$ ($CH_3CN$ 5%→30%, 30 minutes)

Elution velocity: 0.5 mL/min

Temperature for Analysis: 40° C.

UV wavelength for detection: 254 nm

Additionally, salmon sperm DNA (manufactured by Aldrich, 0.68 mg) was dissolved in a 20 mM acetate buffer solution (pH 5.5, 10 mL) of chloroacetaldehyde (manufactured by Tokyo Chemical Industry Co., Ltd., 0.1 M), and the resulting solution was left to stand alone at 37° C. for 72 hours (Deepwell Maximizer manufactured by TAITEC). Methylene chloride (at a volume 2-fold that of the reaction solution) was added for shaking for 15 seconds (TM-252 manufactured by IWAKI) and simply centrifuged for 30 seconds (CHIBITAN-II manufactured by Millipore, 10 krpm). A rinse procedure for removing the organic layer was carried out twice, to obtain modified DNA.

By assaying the mixture of modified and unmodified nucleosides obtained by enzymatic decomposition of the modified DNA, first, the progress of the modification reaction was confirmed.

Figure 10:
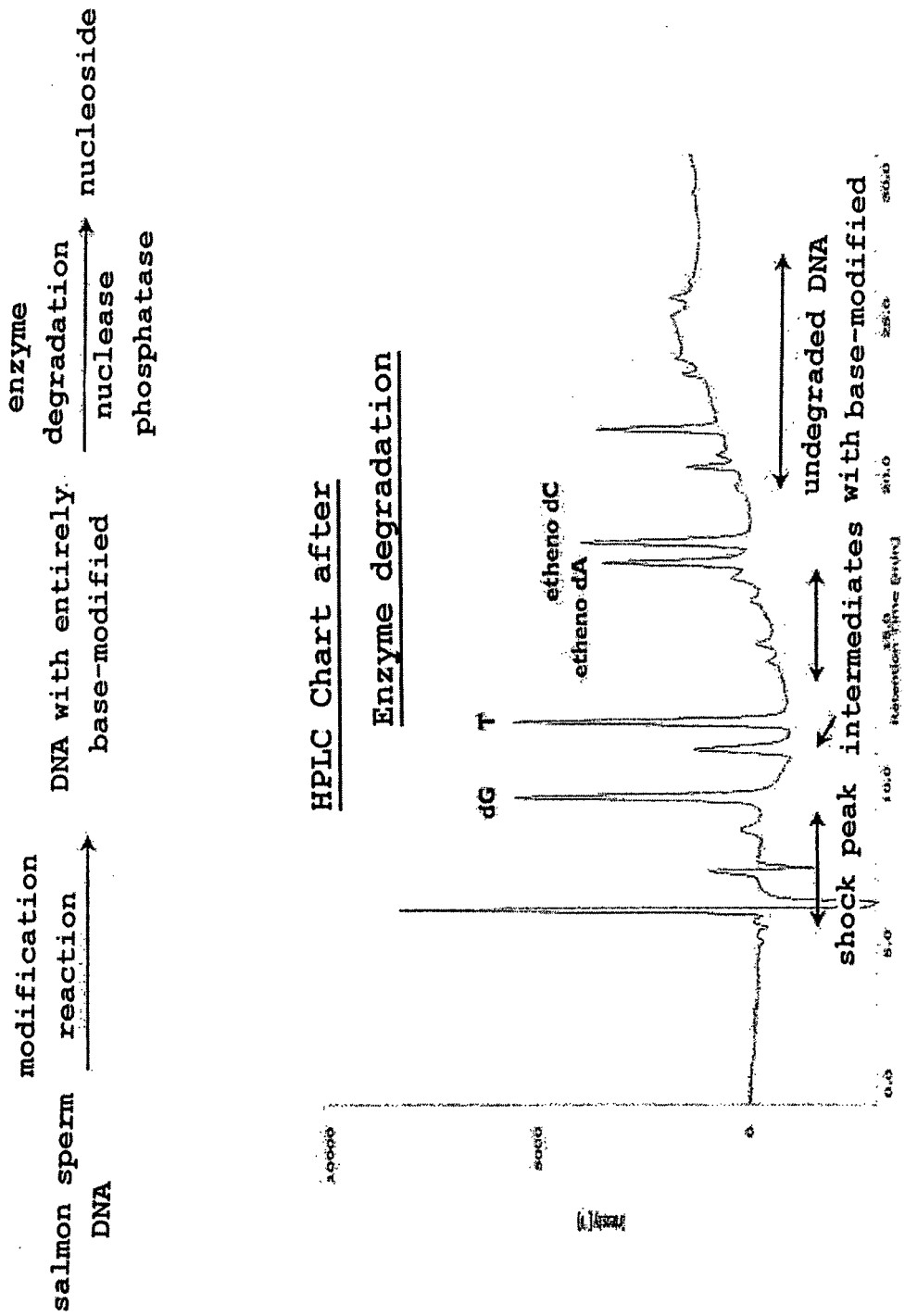
FIG. 10 shows the HPLC chart of the DNA post-modification after enzyme degradation in Example 4 in the second example group.

MilliQ water (42.8 µL) was added to the modified DNA solution (19.1 µL) for dilution, to which a mixture buffer (30 mM sodium acetate, 10 mM zinc chloride, pH 5.3, 5 µl) was added, followed by addition of an aqueous magnesium chloride solution (50 mM, 5 µL). After it was verified that the solution was at pH 5.0, 0.5 µL of an enzyme mixture solution [Nuclease P1 (0.5 unit, manufactured by Wako), DNase I (0.05 unit, manufactured by Takara Bio)] was mixed with the solution; then, 500 mM Tris-10 mM $MgCl_2$ buffer (pH 8.0, 8 µL, manufactured by TOYOBO) was mixed with the resulting solution. After it was verified that the resulting mixture was at pH 8.0, bacterial alkaline phosphatase (0.5 unit, 0.9 µL) was added for shaking at 37° C. for 3 hours (DeepWell Maximizer manufactured by TAITEC). 8.1 µl of aqueous 3.0 M sodium acetate solution and ethanol (224 µL) were added to the reaction solution. The mixture was cooled at −80° C. for 10 minutes followed by centrifugation (15,300 rpm, 10 minutes, Micro-mini cooling centrifuge machine 3615 manufactured by KUBOTA), to recover the supernatant. Furthermore, ethanol (650 µL) was added followed by cooling again at −80° C. for 10 minutes and centrifugation (15,300 rpm, 10 minutes); the resulting supernatant was freeze-dried to obtain the intended mixture of modified and unmodified nucleosides (FIG. 10). Because undigested fragments and reaction intermediates existed therein, no accurate calculation of the reaction efficiency could be done. However, it was shown that the modification reaction proceeded at a high efficiency.

Figure 11:
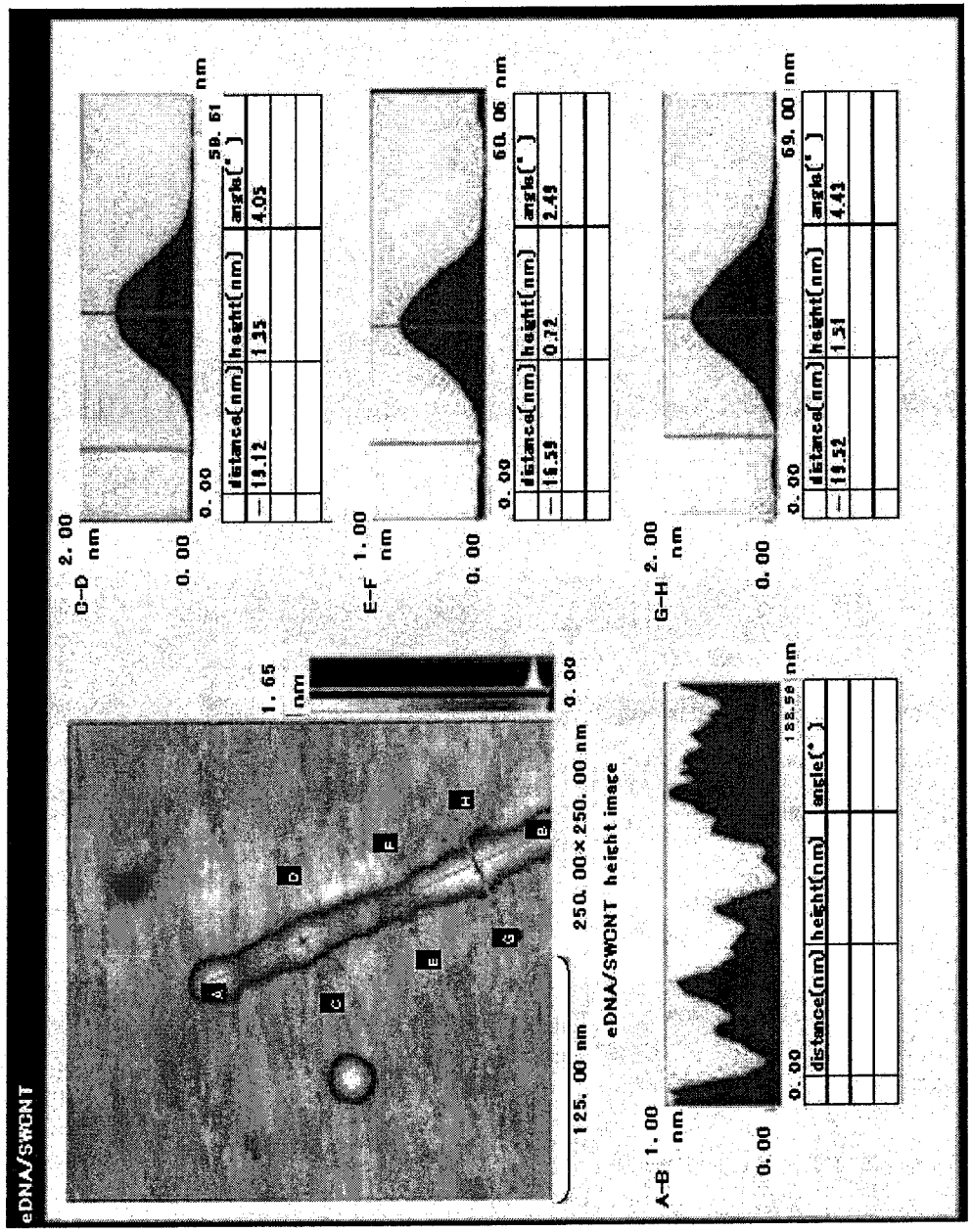
FIG. 11 shows an AFM image of a complex of the modified DNA in Example 4 in the second example group and carbon nanotube. The left photo-picture in FIG. 11 shows an AFM image of a complex of the modified DNA and carbon nanotube; the graph on the right top column shows the histogram between C and D; the graph on the right intermediate column shows the histogram between E and F; and the graph on the right lower column shows the histogram between G and H.
Figure 12:
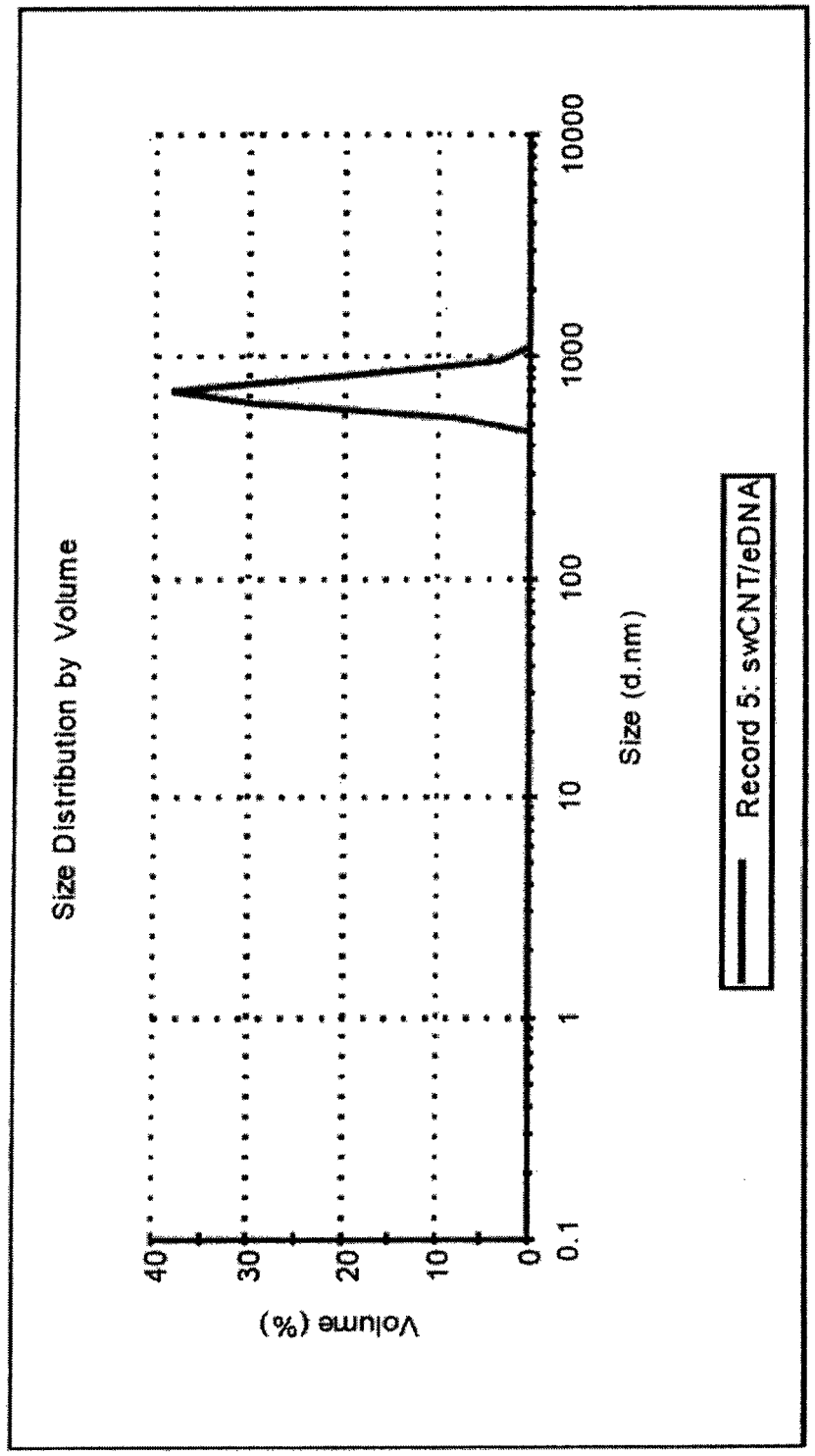
FIG. 12 shows a dynamic light scattering chart of a complex of the DNA post-modification in Example 4 in the second example group and carbon nanotube.

Furthermore, the modified DNA was mixed with monolayer carbon nanotube (SWCNT, HiPco synthetic product, purchased from Sumitomo Shoji, 0.1 mg) for ultrasonic treatment (UT-205S manufactured by SHARP, 5° C., 30 minutes), to adsorb the modified DNA on SWCNT at good dispersibility (FIG. 11). As shown in FIG. 11, the existence of a linear substance as measured with an atomic force microscope (left photo-picture) and the minimum difference 0.8 nm in the height from the base as calculated on the histogram between points E and F on the right middle column indicate the appearance of SWCNT in a single line dispersion under observation; the difference 1.6 nm in the height from the base as calculated on the histogram between points C and D on the right top column and the difference 1.7 nm in the height from the base as calculated on the histogram between points G and H on the right bottom column demonstrate that the modified DNA was adsorbed on the surface of the SWCNT in the single line. Furthermore, the complex of the SWCNT and the modified DNA was subjected to a dynamic light scattering measurement (Zetasizer nano manufactured by Sysmex), so that it was shown that the mean particle size was 700 nm. Since such high dispersibility cannot be obtained from unmodified DNA, the modified nucleic acid obtained by the enlargement modification method is promising as a dispersant of carbon nanotube.

Third Example Group

Second Enlargement Modification Method

The mass spectrometry in the following Example was done under the following conditions.

Apparatus: DE-STR manufactured by Applied Bio
Ionization mode: matrix-assisted laser excitation ionization method (MALDI)
Detection method: fly-time measurement
Laser type: $N_2$ laser
Measurement method: linear
Matrix: 2,4,6-trihydroxyacetophenone
Detection mode: negative An oligonucleotide comprising all of the four essential nucleic acid bases (FIG. 13(1)), namely dAGCT manufactured by Gene Design Inc. was treated by absolutely the same procedures as in the first step in the second example group (1); the resulting modified oligonucleotide (1.1 μmol, FIG. 13(2)) was dissolved in a solution of 3.4 mM p-benzoquinone (manufactured by Aldrich, purity of 98%) in phosphate buffer (0.5 M, pH 7.2, 2,300 μL), for shaking at 37° C. for 24 hours (DeepWell Maximizer manufactured by TAITEC). Methylene chloride (600 mL) was added for shaking for 15 seconds (TM-252 manufactured by IWAKI) and simply centrifuged for 30 seconds (CHIBITAN-II, manufactured by Millipore, 10 krpm). A rinse procedure for removing the organic layer was carried out twice, and then, the resulting aqueous layer was concentrated and dried to obtain the intended modified oligonucleotide shown by the following chemical formula (FIG. 13(3)).

Figure 14:
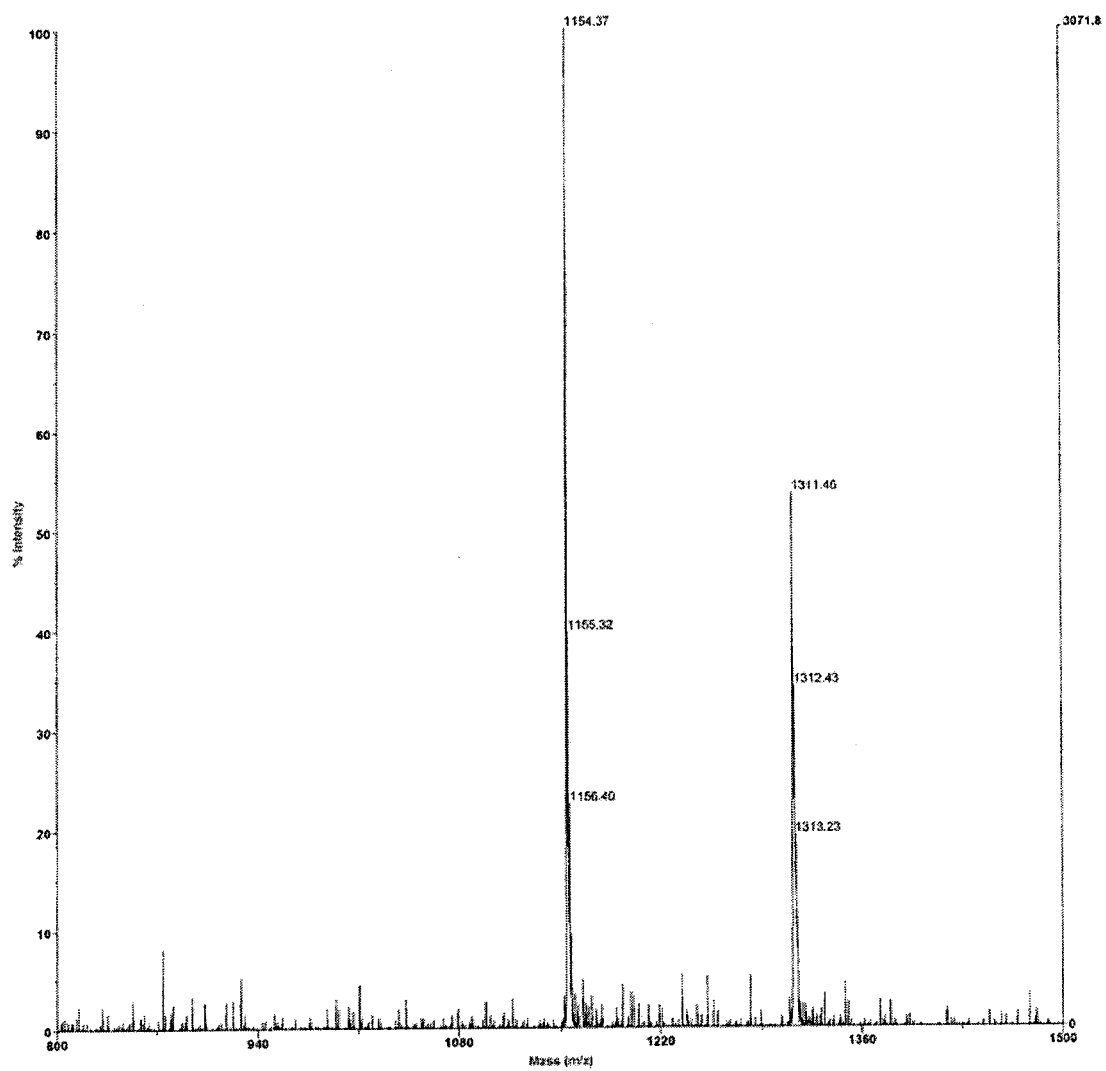
FIG. 14 shows the mass spectrum of the oligonucleotide after the modification at the second step in the third example group.

FIG. 14 shows the mass spectrum of the resulting product. By the mass spectrometry, a main peak was observed at m/z 1311.32 (M−1) close to the calculated value [calculated for $(C_{49}H_{52}N_{15}O_{23}P_3)$ (M−1): m/z 1311.26] (the peak at 1154.37 was from dAGCT as the internal standard).

(Third Step)

The modified oligonucleotide obtained at the second step above was dissolved in hydrochloric acid-acetate buffer (0.5 M, 20 μL). After it was verified that the resulting solution was at pH 2.0, the solution was left to stand alone at 37° C. for 3 hours. The aqueous layer was applied to a gel filtration column (MicroSpin G-25 manufactured by GE HEALTH CARE) to obtain the intended modified oligonucleotide (FIG. 13(4)). The mass spectrum of the product is shown in FIG. 15. By the mass spectrometry, a main peak was observed at m/z 1170.14 (M−1) close to the calculated value [calculated for $(C_{49}H_{52}N_{15}O_{23}P_3)$ (M−1): m/z 1170.21] (the peak at 1311.79 was from an unreactive material).

Fourth Example Group

Third Enlargement Modification Method

Example 1

Modification of dAGCT

The mass spectrometry in the following Example was done under the following conditions.

Apparatus: DE-STR manufactured by Applied Bio
Ionization mode: matrix-assisted laser excitation ionization method (MALDI)
Detection method: fly-time measurement
Laser type: $N_2$ laser
Measurement method: linear
Matrix: 2,4,6-trihydroxyacetophenone
Detection mode: negative An oligonucleotide comprising all of the four essential nucleic acid bases (FIG. 16(1)), namely dAGCT manufactured by Gene Design Inc. was used for the modification reaction.

(First Step)

The oligonucleotide (2.0 mM, 20 μL) was dissolved in an acetate buffer (0.1 M, 164 μL), to which p-benzoquinone (0.6 mg, 5.5 μmol) was added. After the resulting mixture was adjusted to pH 4.5, the mixture was treated at 37° C. for 21 hours. Methylene chloride (328 μL) was added for shaking for 15 seconds (TM-252 manufactured by IWAKI) and simply centrifuged for 30 seconds (CHIBITAN-II manufactured by Millipore, 10 krpm). A rinse procedure for removing the organic layer was carried out twice, and then, the resulting aqueous layer was concentrated and dried to obtain the intended modified oligonucleotide shown by the following chemical formula (FIG. 16(2)).

Figure 17:
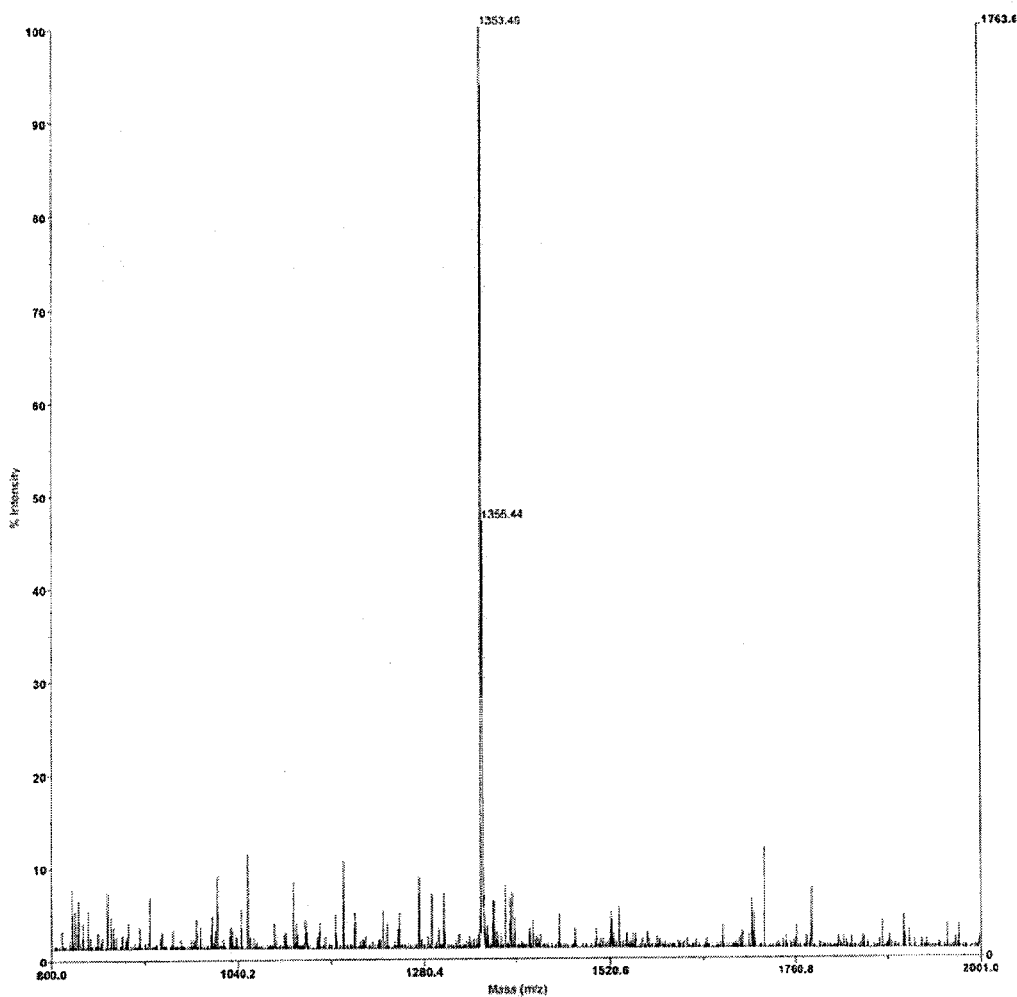
FIG. 17 shows the mass spectrum of the oligonucleotide after the modification at the first step in Example 1 in the fourth example group.

FIG. 17 shows the mass spectrum of the resulting product. By the mass spectrometry, a main peak was observed at m/z 1353.49 (M−1) close to the calculated value [calculated for $(C_{51}H_{54}N_{15}O_{24}P_3)$ (M−1): m/z 1353.27].

(Second Step)

The modified oligonucleotide obtained at the second step above was dissolved in hydrochloric acid-acetate buffer (0.5 M, 20 μL). After it was verified that the resulting solution was at pH 1.0, the solution was left to stand alone at 37° C. for 3 hours. The aqueous layer was applied to a gel filtration column (MicroSpin G-25 manufactured by GE HEALTH CARE) to obtain the intended modified oligonucleotide represented by the following chemical formula (FIG. 16(3)). The mass spectrum of the product is shown in FIG. 18.

By the mass spectrometry, a main peak was observed at m/z 1311.32 (M−1) close to the calculated value [calculated for $(C_{49}H_{52}N_{15}O_{23}P_3)$ (M−1): m/z 1311.26].

When the first step was done at pH 3.0 or less, the modified oligonucleotide from which the modified adenine has been released (FIG. 16(3)) is directly generated.

Example 2

Modification of $dAT_4GT_4CT_4GT_4$

In the following Example, HPLC analysis was done under the following conditions.

Low-pressure gradient pump: PU-2089 Plus manufactured by JASCO Corporation
Sampling unit: AS-950-10
Multi-wavelength UV detector: MD-2015 Plus
Column oven: 860-CO manufactured by JASCO Corporation
Column: COSMOSIL 5C18-ARII manufactured by Nakarai Tesque
Eluent: 0.1 M TEAA buffer (pH 7.0)/$CH_3CN$($CH_3CN$ 5%→30%, 30 minutes)
Elution velocity: 0.5 mL/min
Temperature for Analysis: 40° C.
UV wavelength for detection: 254 nm The mass spectrometry in the following Example was done under the following conditions.

Apparatus: DE-STR manufactured by Applied Bio
Ionization mode: matrix-assisted laser excitation ionization method (MALDI)
Detection method: fly-time measurement
Laser type: $N_2$ laser
Measurement method: linear
Matrix: 2,4,6-trihydroxyacetophenone
Detection mode: negative An oligonucleotide comprising all of the four essential nucleic acid bases (upper image in FIG. 2), namely $dAT_4GT_4CT_4GT_4$ manufactured by Gene Design Inc. was used for the first step alone.

Figure 19:
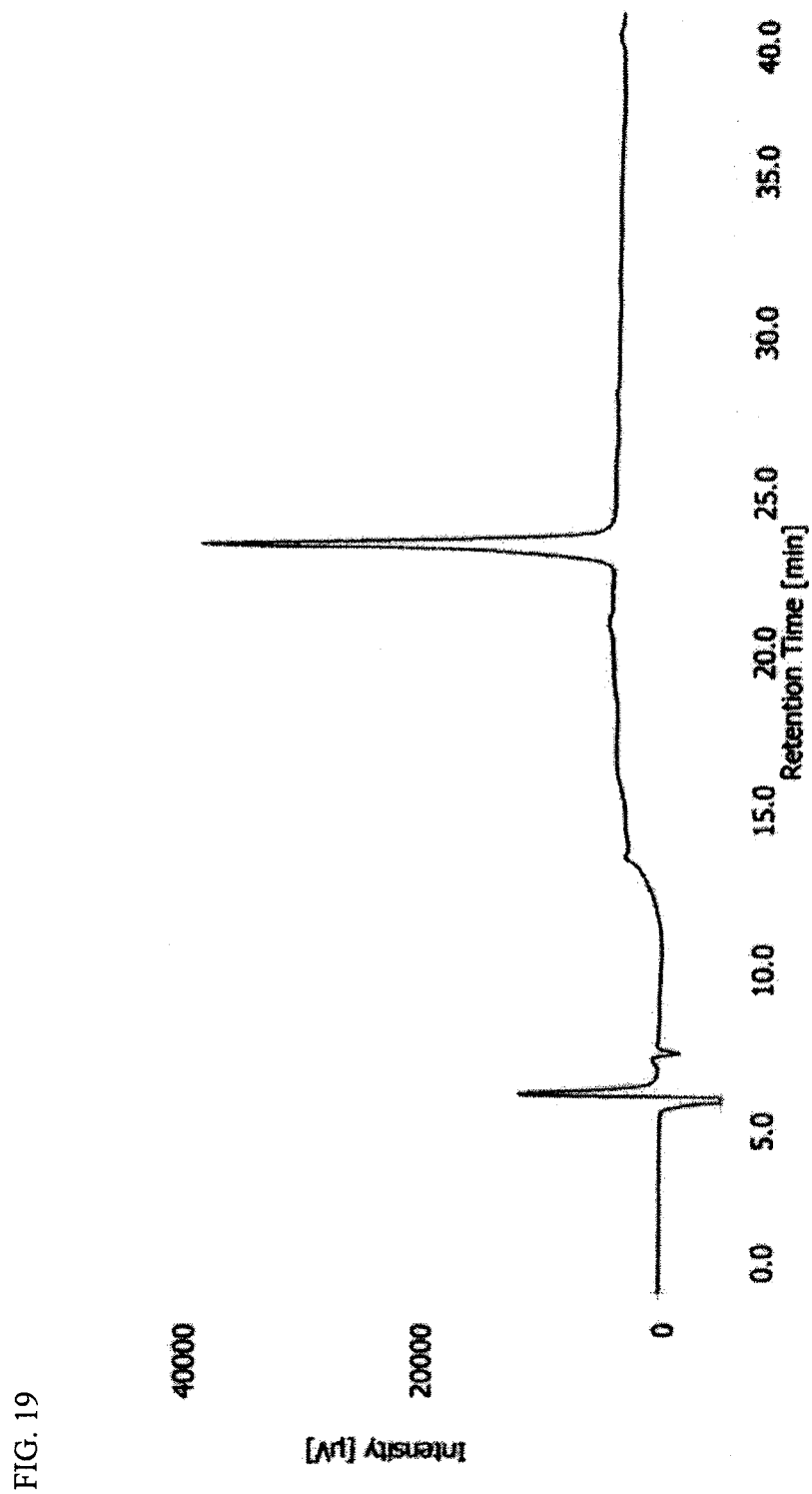
FIG. 19 is the HPLC chart of the oligonucleotide after the modification in Example 2 in the fourth example group.

The oligonucleotide (the number of nucleic acid bases at 80) was dissolved in 60 mM p-benzoquinone-acetate buffer solution (pH 4.5, 0.1 M, 80 mL) for shaking at 37° C. for 40 hours. Methylene chloride (160 mL) was added for shaking for 15 seconds (TM-252 manufactured by IWAKI) and simply centrifuged for 30 seconds (CHIBITAN-II, manufactured by Millipore, 10 krpm). A rinse procedure for removing the organic layer was carried out twice, and then, the aqueous layer was concentrated and dried, to obtain the intended modified oligonucleotide in which all of the adenine (A) and the cytosine (C) in the raw material oligonucleotide were modified. By HPLC analysis of the resulting product (FIG. 19), a single peak was observed. Even by the mass spectrometry, a main peak was observed at m/z 6243.59 (M−1) close to the calculated value [calculated for $(C_{211}H_{261}N_{50}O_{135}P_{19})$ (M−1): m/z 6243.01].

When the reaction proceeds at pH 3.0 or less, a modified oligonucleotide from which the modified adenine is preliminarily eliminated is obtained preferentially.

INDUSTRIAL FIELD OF UTILIZATION

The method for modifying nucleic acid bases and the nucleic acid base-modified product in accordance with the invention are direct approaches in relation with the amplification of the detection sensitivity in obtaining the sequence information of nucleic acid bases and the like. Hence, the development thereof to a technique for analyzing nucleic acid sequence, utilizing various microscopes with resolution below the dimensions of nucleic acid bases, such as transmission electron microscope, scanning tunneling electric current microscope, and atomic force microscope and measurement devices for detecting extremely small electric current change is expected.

Additionally by converting nucleic acid bases to labeled compounds with fluorescence emission properties as in the present approach, the method and the product may be utilized for assaying nucleic acids and the number of nucleic acid bases, with optical microscope and fluorescence plate readers and may also be utilized as a method for examining diseases. By selecting a modification agent, the physico-chemical properties can be controlled by modifying the polarity of a nucleic acid (water soluble, lipid soluble) and the presence or absence of amino group or adding a new functional group. Accordingly, the resulting product has an aspect as a functional substance programmed with the base sequence.

The invention claimed is:

1. A method comprising modifying nucleic acid bases in such a manner that every base species in plural species of bases in a nucleic acid as an oligonucleotide or a polynucleotide can be discriminated while retaining the base sequence.

2. A method according to claim 1, wherein plural species of bases in the nucleic acid are modified by the following reactions (1) or (2) in such a manner that every base species therein can be discriminated:
   (1) base substitution reaction; and
   (2) enlargement reaction of base ring structure.

3. A nucleic acid base-modified product produced by modifying, by a method according to claim 2, a single-stranded nucleic acid as an oligonucleotide or a polynucleotide as a subject for base sequence analysis in such a manner that every base species in plural species of bases in the nucleic acid can be discriminated.

4. A method for modifying nucleic acid bases comprising selectively releasing a specific species of bases among plural species of bases in a nucleic acid comprising plural nucleotide units and then incorporating one single type of a labeling compound in the sites of the specific species of bases.

5. A method for modifying nucleic acid bases according to claim 4, comprising repeating processes of the method for modifying nucleic acid bases for every base species in plural species of bases in a nucleic acid to incorporate labeling compounds of different types depending on the base species, by which every base species can be discriminated from each other and can be detected.

6. A method for modifying nucleic acid bases according to claim 5, wherein the plural species of bases are bases of two types, namely purine bases encompassing at least adenine and guanine and pyrimidine bases encompassing at least cytosine, thymine and uracil.

7. A method for modifying nucleic acid bases according to claim 5, wherein the selective release of a specific species of bases comprises at least any one or more of the following:
   (1) for the selective release of purine bases, a method using H-type cation exchange resins, strong acids, or strong acids in the co-presence of methylation agents;
   (2) for the selective release of pyrimidine bases, a method using hydrazine, or methylhydrazine;
   (3) for the selective release of guanine, a method using Lewis acids, or strong acids in the presence of methylation agents;
   (4) for the selective release of adenine, a method using any of ion exchange resins of HCOOH type, HCl type, $CH_3COOH$ type, $C_6F_5OH$ type, $CCl_2COOH$ type, $CCl_3COOH$ type or $—SO_3H$ type or a method comprising the treatment with aqueous 0.1- to 1 M strong acid solutions, wherein the strong acid includes at least one of hydrochloric acid, sulfuric acid and nitric acid;
   (5) for the selective release of cytosine, a method using mixtures of Lewis acids and strong acids or a method comprising alkylating or acylating the amino group of cytosine and then subjecting the resulting product to a strong acid, or a method comprising interaction with hydrazine in the presence of NaCl; and
   (6) for the selective release of thymine or uracil, a method comprising alkylating or sulfonylating the C=O bond at position 4 or a method comprising harmonized cyclization of the C=C bond at positions 5 and 6 with ethylene or acetylene compounds.

8. A method for modifying nucleic acid bases according to claim 5, wherein the process for incorporating a labeling compound comprises a reducing amination of the hydroxyl group in a base-released site with a labeling amino compound.

9. A method for modifying nucleic acid bases according to claim 8, wherein the labeling amino compound comprises monoaminoundecagold.

10. A method for modifying nucleic acid bases according to claim 8, wherein the labeling amino compound comprises an aminoethanol as a linker for label incorporation by binding to a label, or 1-aminomethylpyrene as a fluorescent dye, quantum dots, spin labels containing at least TEMPO, organic dyes including at least TET, or fluorescent proteins.

11. A nucleic acid base-modified product of a polynucleotide comprising adenine (A), guanine (G), cytosine (C) and thymine (T) or uracil (U), wherein the adenine is converted to a modified adenine represented by the following general formula:

[Chemical formula 1]

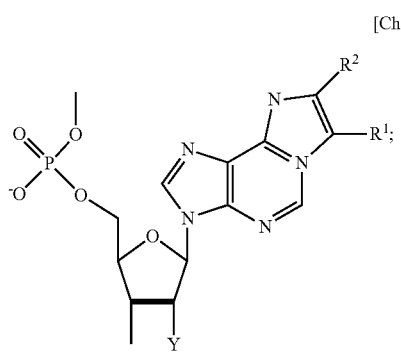

the guanine is converted to a modified guanine represented by the following general formula:

[Chemical formula 2]

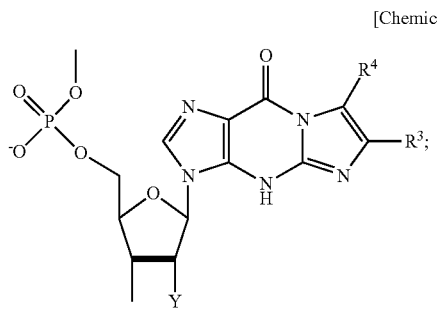

the cytosine is converted to a modified cytosine represented by the following general formula:

[Chemical formula 3]

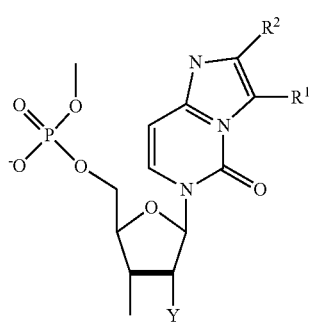

wherein in the formulas, $R^1$ to $R^4$ individually represent hydrogen atom or a hydrocarbon group; $R^1$ and $R^2$ together may form a 5-membered or 6-membered ring; $R^3$ and $R^4$ together may form a 5-membered or 6-membered ring provided that $R^1$ and $R^2$ differ from $R^3$ and $R^4$, and Y represents hydrogen atom or hydroxyl group.

12. A nucleic acid base-modified product according to claim 11, wherein the modified adenine or the modified guanine is converted to a modified product represented by the following general formula:

[Chemical formula 4]

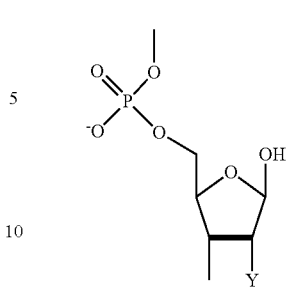

wherein Y represents hydrogen atom or hydroxyl group.

13. A method for modifying nucleic acid bases to produce a nucleic acid base-modified product according to claim 11, comprising a first step of reacting a first halogenated carbonyl compound represented by the following general formula:

CHClR$^1$COR$^2$, wherein $R^1$ and $R^2$ individually represent hydrogen atom or a hydrocarbon group, and $R^1$ and $R^2$ together may form a 5-membered or 6-membered ring, with a polynucleotide comprising adenine, guanine, cytosine and thymine or uracil in an aqueous solution and a second step of reacting a second halogenated carbonyl compound represented by the following general formula:

CHXR$^3$COR$^4$, wherein $R^3$ and $R^4$ individually represent hydrogen atom or a hydrocarbon group, $R^3$ and $R^4$ together may form a 5-membered or 6-membered ring provided that $R^3$ and $R^4$ differ from $R^1$ and $R^2$, X represents Br, I or an alkylsulfonate ester or a benzoquinone derivative represented by the general formula of the following chemical formula 5 wherein $R^5$, $R^6$ and $R^7$ individually represent hydrogen atom or a hydrocarbon group and $R^5$ and $R^6$ together may form a 5-membered or 6-membered ring, with a product resulting from the first step in an aqueous solution adjusted to pH 2.0 to 4.5:

[Chemical formula 5]

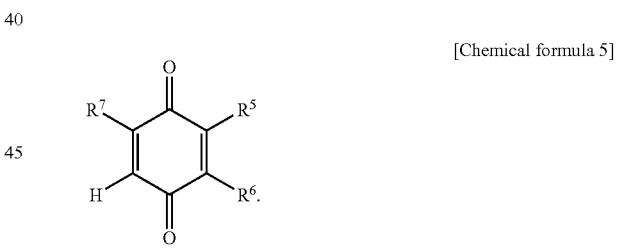

14. A method according to claim 13 for producing a nucleic acid base-modified product represented by the following general formula,

[Chemical formula 4]

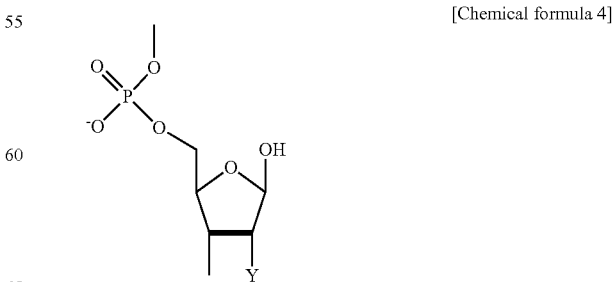

further comprising a step of adjusting the pH to 4.5 to 7.0.

15. A method for modifying nucleic acid bases according to claim 13, wherein the first halogenated carbonyl compound is chloroacetaldehyde while the second halogenated carbonyl compound is 2-bromocyclohexanone or p-benzoquinone.

16. A method for modifying nucleic acid bases, comprising treating a polynucleotide comprising adenine, guanine, cytosine and thymine or uracil with p-benzoquinone at a pH lower than pH 3.0 to induce etheno reaction of the individual bases of adenine and cytosine and simultaneously release the resulting etheno-adenine alone, to obtain a nucleic acid base-modified product shown by the following chemical formula 6:

17. A method for modifying nucleic acid bases, comprising treating a polynucleotide comprising adenine, guanine, cytosine and thymine or uracil with p-benzoquinone at pH 4.5 to pH 6.5 to preferentially induce etheno reaction of the individual bases of adenine and cytosine to obtain a nucleic acid base-modified product shown by the following chemical formula 7:

wherein k, l, m and n individually represent an integer of 0 or more and the total of k, l, m and n is an integer of 2 or more to $3.0 \times 10^8$ or less; additionally, the order of the sequence of nucleotide units represented by k, l, m and n may be any order.

[Chemical formula 6]

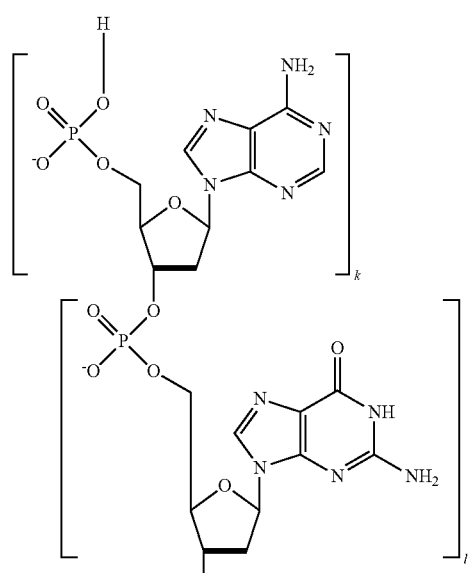
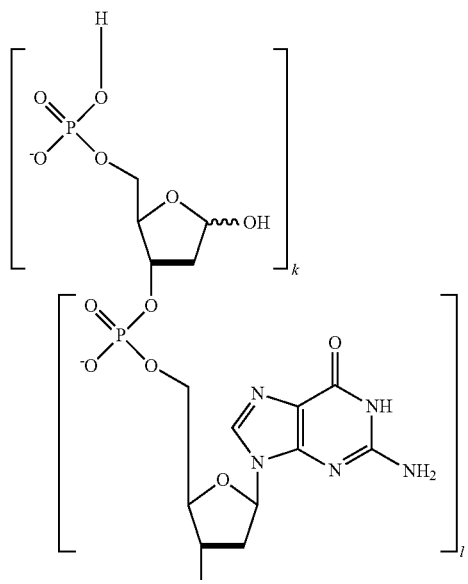
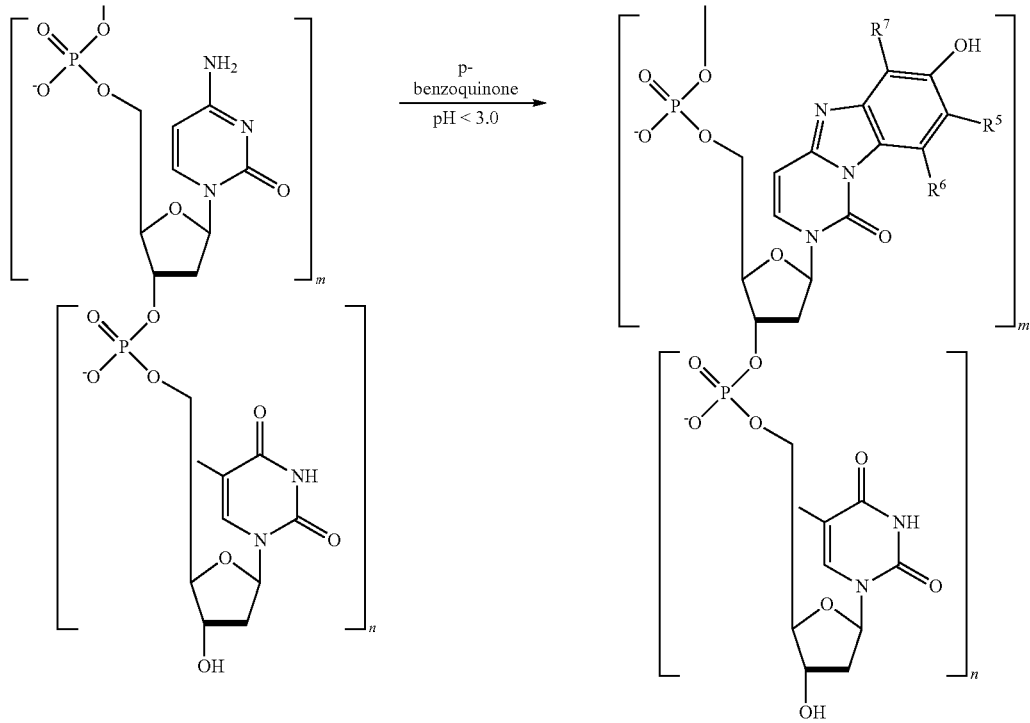

[Chemical formula 7]
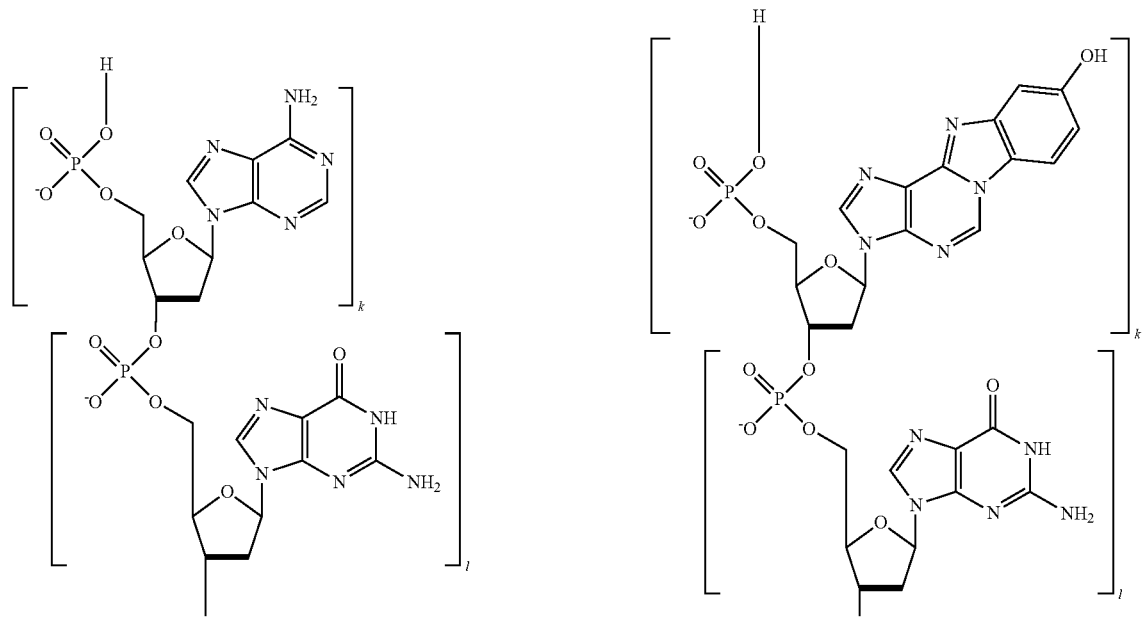
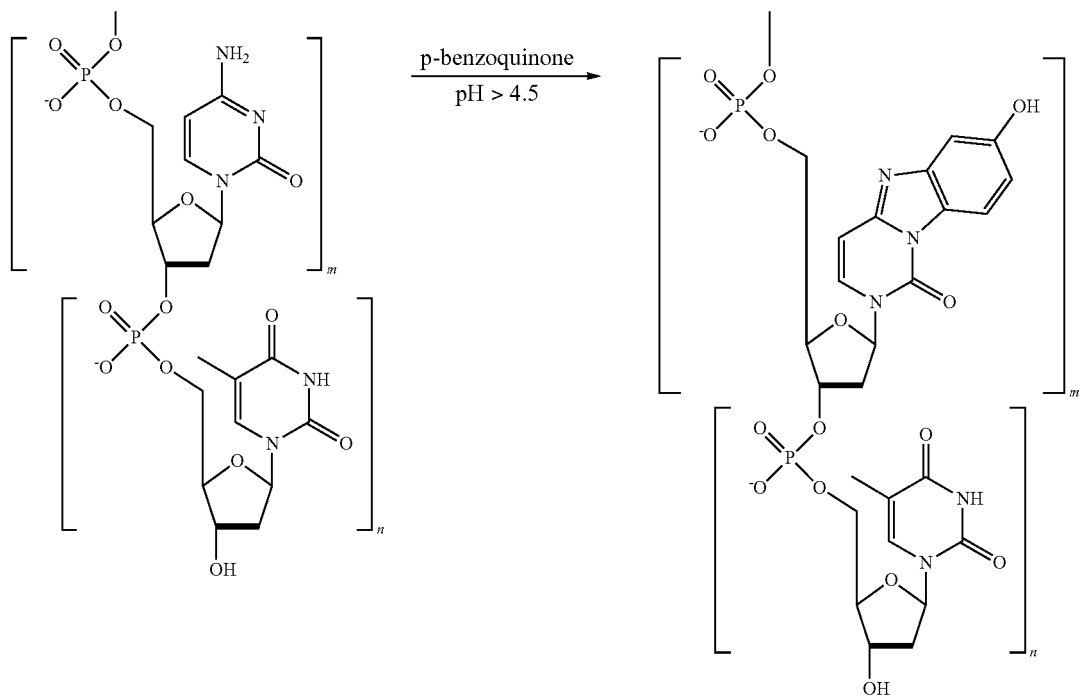
wherein k, l, m and n individually represent an integer of 0 or more and the total of k, l, m and n is an integer of 2 or more to $3.0 \times 10^8$ or less; and the order of the sequence of nucleotide units represented by k, l, m and n may be any order.

18. A nucleic acid base-modified product represented by the chemical formula:
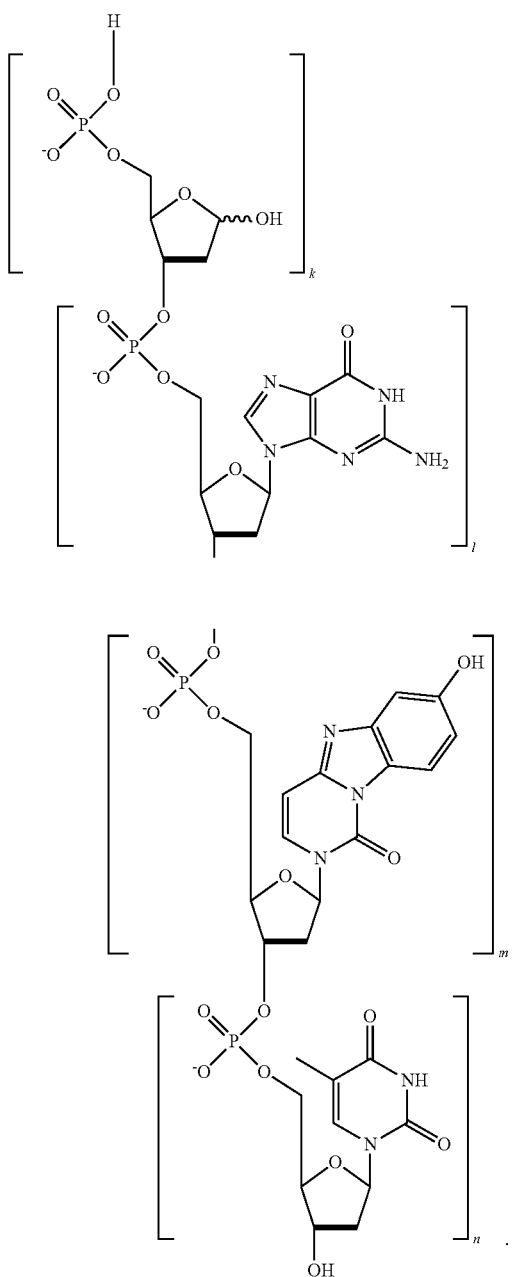
19. A nucleic acid base-modified product represented by the chemical formula:
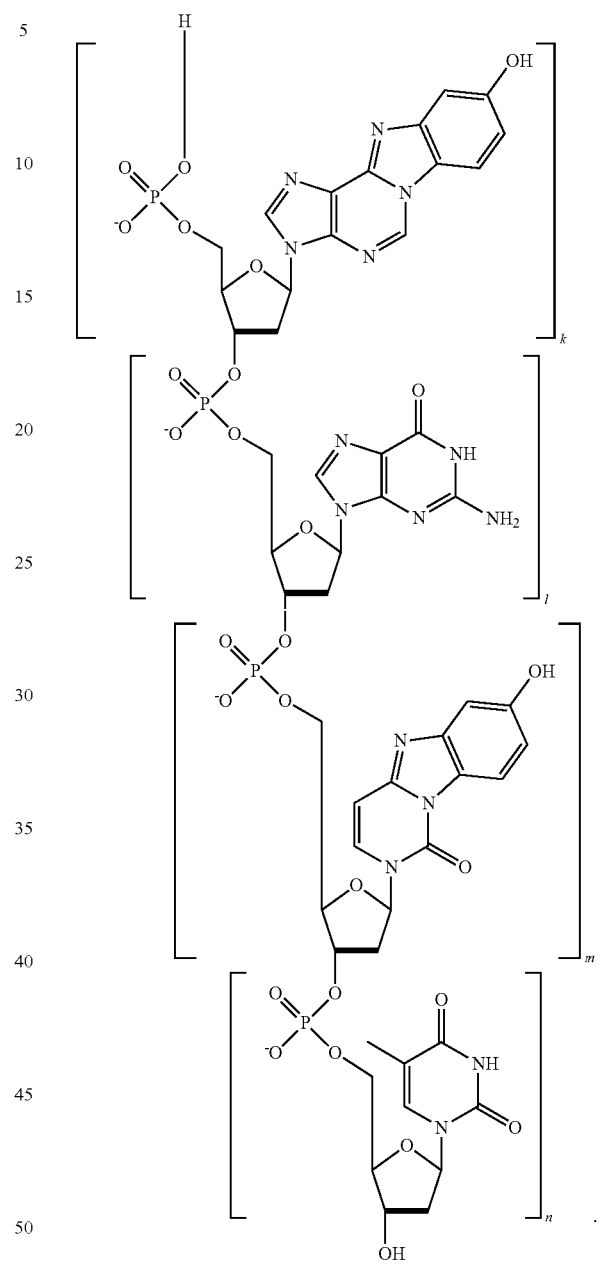
* * * * *